US008999377B2

(12) United States Patent
Rolfes et al.

(10) Patent No.: US 8,999,377 B2
(45) Date of Patent: Apr. 7, 2015

(54) SYSTEM FOR FORMING A BIOCOMPATIBLE FOAM USING POLYMERIZABLE ALPHA(1-4)GLUCOPYRANOSE POLYMERS AND GAS-PRODUCING COMPONENT

(75) Inventors: Emily R. Rolfes, Eden Priarie, MN (US); Stephen J. Chudzik, St. Paul, MN (US); Pamela J. Reed, legal representative, St. Paul, MN (US)

(73) Assignee: Surmodics, Inc., Eden Prairie, MN (US)

( * ) Notice: Subject to any disclaimer, the term of this patent is extended or adjusted under 35 U.S.C. 154(b) by 1658 days.

(21) Appl. No.: 12/284,210

(22) Filed: Sep. 19, 2008

(65) Prior Publication Data

US 2009/0093550 A1  Apr. 9, 2009

Related U.S. Application Data

(60) Provisional application No. 60/994,596, filed on Sep. 19, 2007.

(51) Int. Cl.
| | |
|---|---|
| *A61K 47/36* | (2006.01) |
| *A61K 9/70* | (2006.01) |
| *A61L 15/28* | (2006.01) |
| *C08J 9/00* | (2006.01) |
| *A61K 9/12* | (2006.01) |
| *A61L 15/42* | (2006.01) |
| *A61L 15/62* | (2006.01) |
| *A61L 26/00* | (2006.01) |
| *C08J 9/08* | (2006.01) |

(52) U.S. Cl.
CPC ............... *C08J 9/0004* (2013.01); *A61K 9/122* (2013.01); *A61L 15/28* (2013.01); *A61L 15/425* (2013.01); *A61L 15/62* (2013.01); *A61L 26/0023* (2013.01); *A61L 26/0085* (2013.01); *A61L 26/009* (2013.01); *C08J 9/0061* (2013.01); *C08J 9/08* (2013.01); *C08J 2201/024* (2013.01); *C08J 2303/02* (2013.01); *C08J 2303/14* (2013.01); *C08J 2305/00* (2013.01); *C08J 2305/16* (2013.01); *C08J 2371/02* (2013.01); *C08J 2403/00* (2013.01); *C08J 2405/00* (2013.01); *C08J 2471/00* (2013.01)

(58) Field of Classification Search
None
See application file for complete search history.

(56) References Cited

U.S. PATENT DOCUMENTS

| | | | |
|---|---|---|---|
| 3,081,181 A | 3/1963 | Rutenberg et al. | |
| 4,664,662 A | 5/1987 | Webster | |
| 4,958,015 A * | 9/1990 | Zemel et al. | 536/103 |
| 5,357,012 A | 10/1994 | Nussstein et al. | |
| 5,410,016 A | 4/1995 | Hubbell et al. | |
| 5,645,849 A | 7/1997 | Pruss et al. | |
| 5,686,091 A | 11/1997 | Leong et al. | |
| 5,840,777 A | 11/1998 | Eagles et al. | |
| 5,981,740 A | 11/1999 | Bowen | |
| 6,051,747 A | 4/2000 | Lindqvist et al. | |
| 6,156,345 A | 12/2000 | Chudzik et al. | |
| 6,573,305 B1 | 6/2003 | Thunhorst et al. | |
| 6,599,323 B2 | 7/2003 | Melican et al. | |
| 6,656,974 B1 | 12/2003 | Renn et al. | |
| 6,712,850 B2 | 3/2004 | Vyakarnam et al. | |
| 6,787,682 B2 | 9/2004 | Gilman | |
| 6,884,428 B2 | 4/2005 | Binette et al. | |
| 6,977,323 B1 | 12/2005 | Swenson | |
| 7,025,990 B2 | 4/2006 | Sawhney | |
| 7,112,417 B2 | 9/2006 | Vyakarnam et al. | |
| 7,223,899 B2 | 5/2007 | Sigurjonsson | |
| 7,285,576 B2 | 10/2007 | Hyde et al. | |
| 7,615,036 B2 | 11/2009 | Joshi et al. | |
| 2004/0076811 A1 | 4/2004 | Sato | |
| 2005/0176834 A1 | 8/2005 | Hintz et al. | |
| 2006/0029675 A1 | 2/2006 | Ginther | |
| 2007/0065481 A1 | 3/2007 | Chudzik et al. | |
| 2007/0065484 A1 * | 3/2007 | Chudzik et al. | 424/426 |
| 2007/0254016 A1 | 11/2007 | Andersen et al. | |
| 2008/0033392 A1 | 2/2008 | Gaserod et al. | |

FOREIGN PATENT DOCUMENTS

| | | | |
|---|---|---|---|
| CH | 653351 | A5 | 12/1985 |
| EP | 0594148 | A1 | 4/1994 |
| EP | 0691113 | A1 | 10/1996 |
| EP | 0 812 877 | A2 | 6/1997 |
| EP | 1645298 | B1 | 12/2006 |
| WO | 92/13576 | A1 | 8/1992 |
| WO | 93/09176 | | 5/1993 |
| WO | 00/045871 | | 8/2000 |
| WO | 03/039419 | A2 | 5/2003 |
| WO | 2004/039421 | A1 | 5/2004 |
| WO | 2004/062704 | A1 | 7/2004 |
| WO | 2007/103208 | A2 | 9/2007 |
| WO | 2008/043364 | A1 | 4/2008 |

OTHER PUBLICATIONS

PCT Search Report for International Application No. PCT/US/2008/010928; mailed Nov. 28, 2008.

Artursson et al. (1984) Characterization of Polyacryl Starch Microparticles as Carriers for Protein and Drugs. Journal of Pharmaceutical Sciences, 73:1507-1513.

Chen et al. (2004) Starch Graft Poly(methyl acrylate) Loose-Fill Foam: Preparation, Properties and Degradation. Biomacromolecules, 5:238-244.

(Continued)

*Primary Examiner* — Kevin S Orwig
(74) *Attorney, Agent, or Firm* — Kagan Binder, PLLC

(57) ABSTRACT

Biocompatible foams having excellent physical and chemical properties are described. The biocompatible foams can be formed in situ or applied as a pre-formed foam for the treatment of tissue. The invention provides biocompatible degradable foams formed with a poly-α(1→4)glucopyranose macromer. The invention also provides biostable foams formed with a poly(alkylene oxide) macromer.

23 Claims, 5 Drawing Sheets

(56) References Cited

OTHER PUBLICATIONS

El-Tahlawy et al. (2007) Aspects of the preparation of starch microcellular foam particles crosslinked with glutaraldehyde using a solvent exchange technique. Carbohydrate Polymers, 67: 319-331.

Nayak et al. (2001) Macroporous copolymer matrix IV. Expanded bed absorption application. Journal of Chromatography A, 922: 63-76.

* cited by examiner

US 8,999,377 B2

SYSTEM FOR FORMING A BIOCOMPATIBLE FOAM USING POLYMERIZABLE ALPHA(1-4)GLUCOPYRANOSE POLYMERS AND GAS-PRODUCING COMPONENT

CROSS-REFERENCE TO RELATED APPLICATION

This application claims the benefit of U.S. Provisional Patent Application Ser. No. 60/994,596, filed Sep. 19, 2007, entitled WOUND TREATMENT COMPOSITIONS AND METHODS USING POLYMER FOAMING, the disclosure of which is incorporated herein by reference.

FIELD OF THE INVENTION

The invention relates to biocompatible polymer foams, and compositions and methods for forming them. The invention also relates treatment of tissue and wound sites using in situ- or pre-formed foams.

BACKGROUND

Various medical techniques have been used to treat tissue disruptions, including wounds to dermal tissue and disruptions to tissues in other parts of the body. Some objectives for the treatment of wounds are to achieve wound closure and promote the proper formation of new tissue at the wound site. Without some type of medical intervention it can be very difficult for the body to heal a wound in a manner that results in minimal subsequent tissue alteration. If the extent of damage to underlying vascular tissues is significant, vascularization is compromised and oxygen cannot be supplied to the wound in sufficient quantities for good healing. Infection at the wound site can also create problems and slow down cellular processes involved in the healing process. In some cases other body problems (ulcers) make it difficult for the healing process to proceed leading to chronic wounds.

Conventional methods that facilitate wound healing involve the use of wound dressings. Currently, numerous occlusive types of wound dressings are used or suggested for treatment. These include polyurethane films, hydrocolloidal particles bound to polyurethane foams, hydrogels, hydrophilic and hydrophobic foams, nonwoven composites of fibers from calcium alginate, and cellophane.

More recent interest for the treatment of wounds, especially deep or cavernous wounds, has focused on compositions that polymerize and foam in situ. These compositions are able to produce a one-piece absorbent foam and fill the wound. Success of these in situ compositions and treatments however, has been limited. Foam forming systems contemplated for in situ wound treatment suffer from one or more of the following drawbacks: lack of biocompatible foam forming materials or foamed product; expensive materials; significant foam set-up times; and insufficient structural properties of formed foams (such as porosity, structural integrity, strength, and flexibility).

Although it is believed that porous foamed materials can be useful for tissue healing, many traditional techniques for producing foams do not use biocompatible starting materials. For example, although polyurethane foams are widely used in various areas of technology, there are fundamental concerns with the biocompatibility of the components used to make polyurethane foams. The preparation of foamed polyurethanes generally involves the use of diisocyanates, which can be toxic and can cause a significant inflammatory response. Toxic catalytic systems have also been used for the preparation of polyurethane foams. Even the application of pre-formed polyurethane foams to tissue can be problematic if unreacted diisocyanate material is present in the foam and leeches into tissue intended to be treated. Furthermore, polyurethane forms are generally not biodegradable over periods of time useful for tissue healing processes.

Another challenge for the preparation of biocompatible foams relates to the reaction chemistries needed to produce a crosslinked matrix of polymeric materials and gas bubbles as the polymeric materials crosslink to form the foam. The production of polyurethane foams from isocyanate starting materials is typically robust and reliable, resulting in well formed porous foams. Polyurethane foams are typically prepared by the reaction of isocyanates with active hydrogen-containing compounds (such as polyhydric alcohols), in the presence of small quantities of water. Urethane polymer formation of isocyanates with alcohols is accompanied by the production of gas. The gas required from the foam production comes from the carbon dioxide produced from the reaction of the isocyanate group with water. The carbon dioxide diffuses into bubbles in the reaction mixture and causes expansion of the polymerizing material to make a foam. The gas-producing reaction is linked to the polymerization reaction (and thereby occurs simultaneously).

However, the production of foams using non-isocyanate chemistries can be considerably more difficult. In many other systems, the chemistry of crosslinking of the polymeric materials is not linked to the chemistry of gas bubble production. This, in turn, makes the production of other types of polymeric foams considerably more challenging, especially where it is desired to form the foams on a tissue site in a short period of time.

Crosslinked collagen-mucopolysaccharide composites have been described as materials suitable for the production of porous foams. In these foams, the mucopolysaccharide used is alginate, which can becomes ionically crosslinked using a cation, such as calcium. In terms of biocompatibility, these materials can provide an improvement over materials used to make polyurethane foams, but suffer from a number of shortcomings. For example, foams produced from collagen-alginate materials can have rather poor porous structures. Collagen-alginate foams produced using conventional techniques (see, for example, U.S. Pat. No. 5,840,777) are often very thin (less than 5 mm) with thicker structures becoming prone to collapsing upon itself. In addition, for in situ application, cationic crosslinking of the collagen-alginate materials can take a considerable period of time (e.g., from two to five minutes). This may be unacceptable in many medical procedures where the material is desired to foam very quickly (such as in a period of time of less than 20 seconds). Furthermore, with this slow crosslinking it can be difficult to coordinate gas generation with polymerization. Gas may escape from the compositions as the materials ionically crosslink, resulting in an insufficient porous structure.

Because of these problems collagen-alginate foams are preferably made by freeze drying. Freeze drying techniques, however, are not practical for the production of in situ formed foams. Freeze dried foams also suffer the disadvantage of shrinking considerably and irreversibly when brought into contact with liquids, such as an aqueous solution. Such shrinkage causes closure of the pores and makes the material less useful in the applications where the high level of porosity is required or preferable. The problems of shrinkage and pore collapse suffered by crosslinked collagen-mucopolysaccharide materials are not unique to the materials. A wide variety of natural and synthetic polymers also suffer these mechanical problems when placed in contact with liquids. Furthermore, a foam created from crosslinked collagen-alginate materials can be very difficult to degrade when placed in contact with tissue.

SUMMARY

The present invention relates to biocompatible polymer foams, compositions and methods for the preparation of the foams, and methods for using the polymer foams. The inventive foams are formed from certain biocompatible macromers in combination with a polymerization initiator and gas generation components. The biocompatible polymer foams can be used in association with a target tissue for its treatment. The biocompatible polymer foams can be formed at the site of treatment (e.g., in situ formation of the foam) or can be pre-formed, and then associated with a target tissue. The biocompatible polymer foams can be biostable or biodegradable.

The invention overcomes challenges associated with the preparation of biocompatible foams that are formed from polymerizable components, wherein the gas generating mechanism in the foam-forming system is not necessarily chemically coupled to the mechanism driving polymerization. In other words, the components of the gas-generating system can be activated and operate independently of the activated polymerization initiators. In a foam-forming system with this type of "uncoupled" gas generation-polymerization initiation mechanism, the formation of foams with desirable properties (e.g. porosity, strength, etc.) is very challenging because it is very difficult to coordinate gas generation with polymerization of the matrix forming materials. Despite these challenges, the invention provides foam-forming systems having an inventive combination of highly soluble foam-forming polymerizable polymeric components and a gas generating system. Used together, these components of the invention form biocompatible foams having excellent structural properties.

In one embodiment, the invention provides a system for forming a biocompatible biodegradable foam, the system comprising a covalently crosslinkable polymer comprising poly-α(1→4)glucopyranose and pendent polymerizable groups, a polymerization initiator, and a gas-producing component.

In a related embodiment, the invention also provides a method for forming the biocompatible biodegradable foam, which comprises steps of disposing a composition comprising a covalently crosslinkable polymer comprising poly-α(1→4)glucopyranose and pendent polymerizable groups; a polymerization initiator; and a gas-producing component, wherein the gas-producing component reacts to produce gas and the polymerization initiator is activated to cause polymerization and formation of a foam. For example, the composition can be disposed and formed on a target tissue, such as a dermal wound or on bone.

In a related embodiment, the invention also provides a formed biocompatible biodegradable foam comprising a crosslinked polymeric matrix comprising poly-α(1→4)glucopyranose. The foam has excellent initial structural integrity and can be enzymatically degraded. Optionally, the foams can be degraded enzymatically and by hydrolysis. In more specific embodiments the biocompatible biodegradable foam can have one or more of the following properties: a pore volume in the range of 1.5 to 7.5, a compressive modulus in the range of 0.5 kPa to 50 kPa, and/or a 50% compressive force in the range of 0.5 N to about 20 N.

In more specific embodiments, the biocompatible biodegradable foams, systems or methods include one or more of the following features: poly-α(1→4)glucopyranose having a molecular weight of 500,000 Da or less, a polymerizable group loading of in the range of about 0.05 mmol/gram to about 0.4 mmol/gram polymer, and/or a polymer final concentration in the range of about 200 mg/mL to about 1000 mg/mL, and/or a polymer final concentration in the range of about 400 mg/mL to about 700 mg/mL.

In other specific embodiments, the biocompatible biodegradable foams are formed using a second hydrophilic biocompatible macromer in addition to the poly-α(1→4)glucopyranose macromer. In favored aspects, the second macromer is a biocompatible biostable alkylene oxide polymer having pendent polymerizable groups. In more specific embodiments, the biocompatible biodegradable foams, systems or methods include one or more of the following features: a weight ratio of poly-α(1→4)glucopyranose to second macromer in the range of about 1:1 to about 3:1, or about 1:1 to about 2:1

In aspects relating to biocompatible biodegradable foams, the foams can degrade over a period of time at a target site, but that maintain desirable physical properties during the degradation period. For example, the foam structure is maintained for a significant portion of the foam's lifetime at the tissue site. In other words, pores of the biodegradable foams do not collapse soon after the materials of the foam begin to degrade. For example, the poly-α(1→4)glucopyranose is gradually enzymatically degraded, which causes a thinning of the walls of the foam's cellular structure. The degraded (and sometimes disassociated) solids materials from the foam are absorbed by the body, and gradually, the foam structure is replaced by regenerated tissue. This offers an advantage for tissue healing, as cells and tissue in-growth will continue to occur over the degradation period. By comparison, foams made using other polymeric systems may collapse quickly, or may have an insufficient rate of degradation at the target site. Optionally, before the foam is completely degraded, it may be removed from the tissue site.

Other embodiments of the invention relate to biocompatible biostable foams, systems and methods for forming biocompatible biostable foams, and methods for treating tissue using the biocompatible biostable foams. Biostable foams formed at the tissue site may either be left to become a permanent part of the body, or removed after a period of treatment. If the biostable foam is left at the target site it can offer at least a partial structural replacement of the tissue (such as bone) that is naturally at the site.

In another embodiment, the invention provides a system for forming a biocompatible biostable foam, the system comprising a covalently crosslinkable branched hydrophilic polymer, a second hydrophilic biocompatible linear macromer, a polymerization initiator, and a gas-producing component. In favored aspects, the second macromer is a biocompatible biostable alkylene oxide polymer having pendent polymerizable groups. In favored aspects, the covalently crosslinkable branched hydrophilic polymer comprises a covalently crosslinkable branched alkylene oxide polymer.

In a related embodiment, the invention also provides a method for forming the biocompatible biostable foam, which comprises steps of disposing a composition comprising the covalently crosslinkable branched hydrophilic polymer, the second biocompatible linear hydrophilic macromer, a polymerization initiator, and a gas-producing component, wherein the gas-producing component reacts to produce gas and the polymerization initiator is activated to cause polymerization and formation of a foam. For example, the composition can be disposed and formed on a target tissue, such as a dermal wound or on bone. After the desired period of use, the foam can be left is association with the target tissue, or removed.

In a related embodiment, the invention also provides a formed biocompatible biostable foam comprising a polymeric matrix comprising biocompatible branched and linear hydrophilic polymeric segments crosslinked via reacted polymerizable groups. Favorably, the polymeric matrix comprises branched alkylene oxide polymer and hydrophilic linear segments crosslinked via reacted polymerizable groups. In more specific embodiments the biocompatible biodegradable foam can have one or more of the following properties: a pore volume in the range of 1.5 to 7.5, a compressive modulus in the range of 5 kPa to about 200 kPa, and/or a 50% compressive force in the range of 1 N to 50 N. Exemplary levels of derivation are in the range of about 0.001 to about 0.01 mol polymerized groups per gram of polymer.

In more specific embodiments, the biocompatible biostable foams, systems or methods include one or more of the following features: a linear and a branched alkylene oxide polymer comprising poly(ethylene glycol) and/or poly(propylene glycol), both linear and branched alkylene oxide polymers having a molecular weight of 10,000 Da or less, or a combined polymer concentration in the range of about 400 to about 700 mg/mL.

In some preferred aspects, the polymerization initiator comprises members of a redox pair, that, when combined, initiate polymerization of the polymerizable component. Exemplary redox pairs include activating agents that are salts and derivatives of electropositive elemental metals; exemplary initiating agents include peroxides, metal oxides, and oxidases. The system can also be formulated to provide compositions that foam and solidify rapidly, as well as those that foam and set up or polymerize slowly.

In some preferred aspects, the gas-producing component comprises compounds of a reactive pair, that, when combined, result in gas being liberated. Exemplary reactive pairs include acids and bicarbonate salts.

In one preferred aspect, the system comprises two compositions, that when combined, cause simultaneous polymerization initiation of the macromers, as well as gas generation. In this regard, in another aspect, the invention provides a system for the in-situ treatment of a wound site that includes a first composition comprising a first member of a redox pair that is an activating agent, and an acid; and a second composition comprising a second member of a redox pair that is an initiator agent, and a gas-releasing compound that releases gas upon contact with the acid, the gas-releasing compound being present in a foam-forming amount. In either the first or second composition, or both, there is a biocompatible polymerizable component. The first and second compositions can be combined and used in-situ to form polymerized foam article for the treatment of the wound site.

The system can also include a mixing device that facilitates combination of the first and second compositions. Accordingly, the invention provides a kit for the treatment of a wound site including two separate compositions and a mixing device. In the kit, the components of the system can be combined in the mixing device.

The invention also provides biocompatible foam-forming systems having particular polymerization initiator and/or gas-producing components which enhance the formation of the foams. According to the experimental studies associated with the invention, it has been found that selected polymerization activators are beneficial for forming rapidly setting, well-formed foams. Therefore, in another embodiment, the invention provides a system for forming a biocompatible foam, the system comprising a covalently crosslinkable polymer comprising pendent polymerizable groups, a polymerization initiator comprising an activating component selected from the group consisting of ferrous gluconate, ferrous ascorbate, ferrous acetylacetonate, and ferrous lactate, and a gas-producing component.

In other experimental studies it was found that well formed biocompatible foams could be formed using a peroxide-based initiator agent. The use of a peroxide-based initiator is somewhat counterintuitive for tissue-based applications, because it is thought that the presence of free hydroxyl radicals would be damaging to tissue. However, it was determined that hydrogen peroxide could be used in a foam forming composition with little or no detrimental affects to cells, while at the same time useful for making a foam having properties desirable for tissue treatment. Therefore, in another embodiment, the invention provides a system for forming a biocompatible foam, the system comprising a covalently crosslinkable polymer comprising pendent polymerizable groups, a polymerization initiator comprising a peroxide initiator agent, and a gas-producing component.

In yet other experimental studies it was found that well-formed biocompatible foams could be created using particular surfactants in combination with an alkylene oxide-based macromer. Although the use of surfactant is optional, it has been found beneficial with these types of macromer components. Poloxamer-type surfactants, which have chemical similarities with the alkylene oxide-based macromers, were used to form several examples of the biocompatible foams and facilitated the formation of excellent foamed structures. Therefore, in another embodiment, the invention provides a system for forming a biocompatible foam, the system comprising a covalently crosslinkable alkylene oxide polymer comprising pendent polymerizable groups, poloxamer based surfactant, a polymerization initiator, and a gas-producing component.

In some modes of practice, the components of the system are mixed and then applied in situ as an application composition to a tissue site on or in a subject. In the course of the mixing and/or application, the components in the composition produce a gas while polymerization of the polymerizable components takes place. In other modes of practice, the components of the system are mixed away from the body to form a pre-formed foam. The pre-foamed polymeric articles can have a shape and configuration suitable for the treatment of tissue at a target location. The pre-formed foams can then be associated with tissue for its treatment.

Whether in situ-formed or pre-formed, one advantage is that the composition of the invention can very rapidly form a polymerized foam with desirable properties. In many aspects of the invention, foam set-up takes place in less than about 20 seconds, less than 10 seconds, and even in less than 5 seconds (although the compositions of the invention can be tuned for longer foam set-up times). After this very short set-up period, the foam is fully cured and functional for tissue treatment. This can improve a surgical procedure wherein the foam is formed, requiring the user to spend a minimal mount of time waiting for the polymerization of the foam to take place. In turn, this improves aspects associated with the sterility of the procedure. Further, the short set-up period minimizes the loss of components from the application site.

The foams of the invention have one or more desirable properties (e.g., porosity, uniformity, thickness, strength, and/or flexibility) that are highly beneficial for the treatment of tissue. In some aspects, the foam can have a porous structure which allows the in-growth of cells into the foam. In some aspects the foam can have a porous structure of high uniformity in terms of pore size and spacing. The formed foam can also have a structure that is resistant to collapse during or after its formation. As such, the compositions and methods of present invention allow the formation of biocompatible foams having dimensional attributes (e.g., depth, width) that are considerably greater than those described in the prior art. The inventive process and composition can be performed to completely fill a treatment site with the foam of the invention, and a porous structure is present throughout the foam. In many cases the treatment or wound site has considerable depth (e.g., greater than 5 mm), which can be up to multiple centimeters deep, and can also be considerably wide and long. For example, in terms of volume, the foams may occupy a space up to tens of cubic centimeters. This is advantageous in wound-healing applications where individual wounds have unique depths and shapes of are unique. The ability to form a foam having a porous structure is present throughout in treatment sites of these sizes represents a significant improvement in the technologies of biocompatible foams and tissue regeneration. The porous structure of the inventive foams can be described in terms of pore volume, which is the ratio of the foam's air volume to the foam's total volume. In some aspects the biocompatible foams of the invention have a pore volume in the range of about 7.5 to about 1.5. The porous structure of the inventive foams can also be described in terms of strength of withstanding collapse under a low-pressure environment.

The system can also include optional components that may improve tissue healing. The components can include bioactive agents such as growth factors which promote cellular processes leading to the formation of functional tissue. In some aspects, the bioactive agent is releasable from a biodegradable foam upon its degradation.

DETAILED DESCRIPTION

Figure 1:
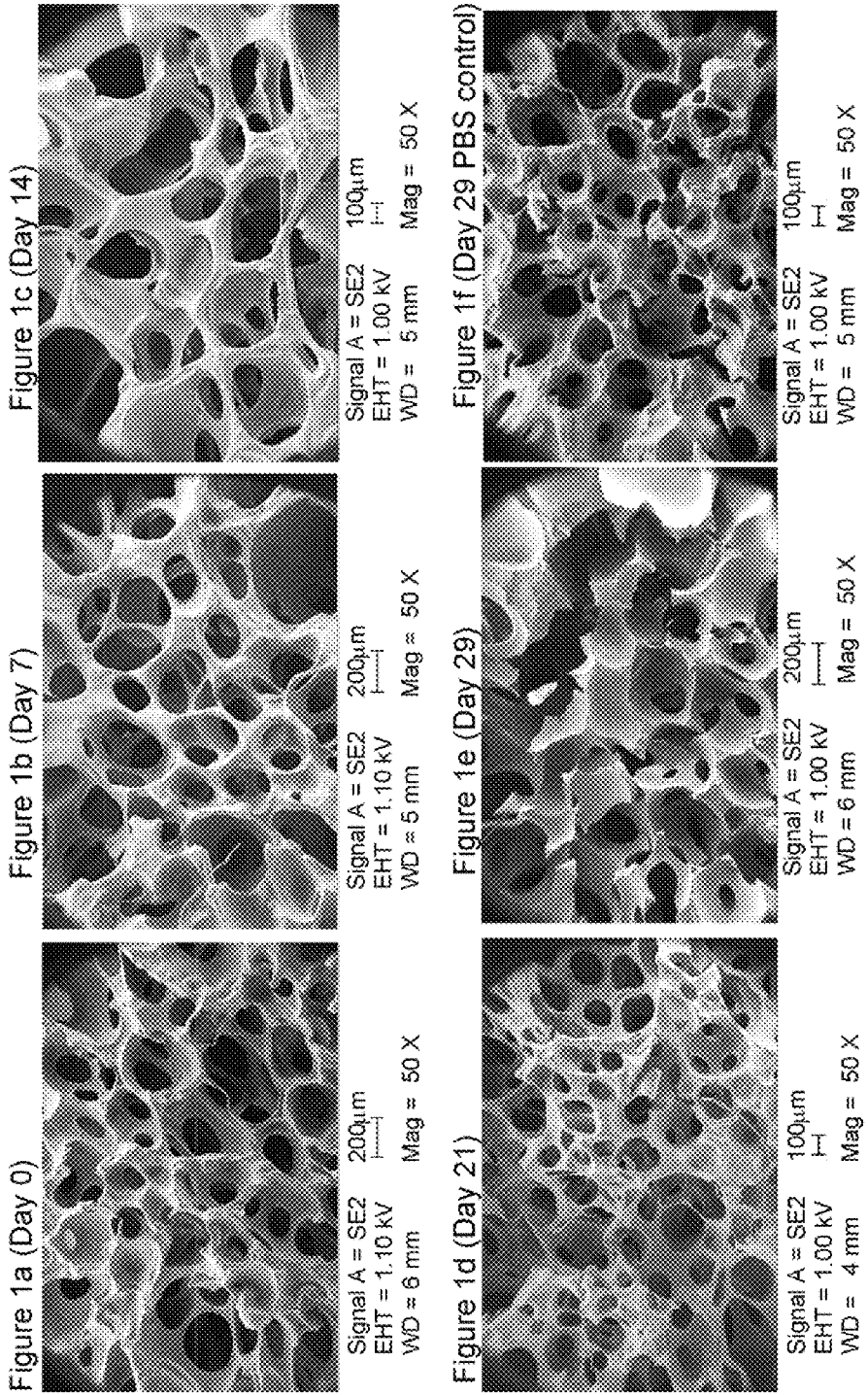
FIGS. 1a-1e are scanning electron micrograph (SEM) images of biodegradable maltodextrin/poly(ethylene glycol) foams at time periods following exposure to amylase; 1f is micrograph (SEM) image of a control.
Figure 2:
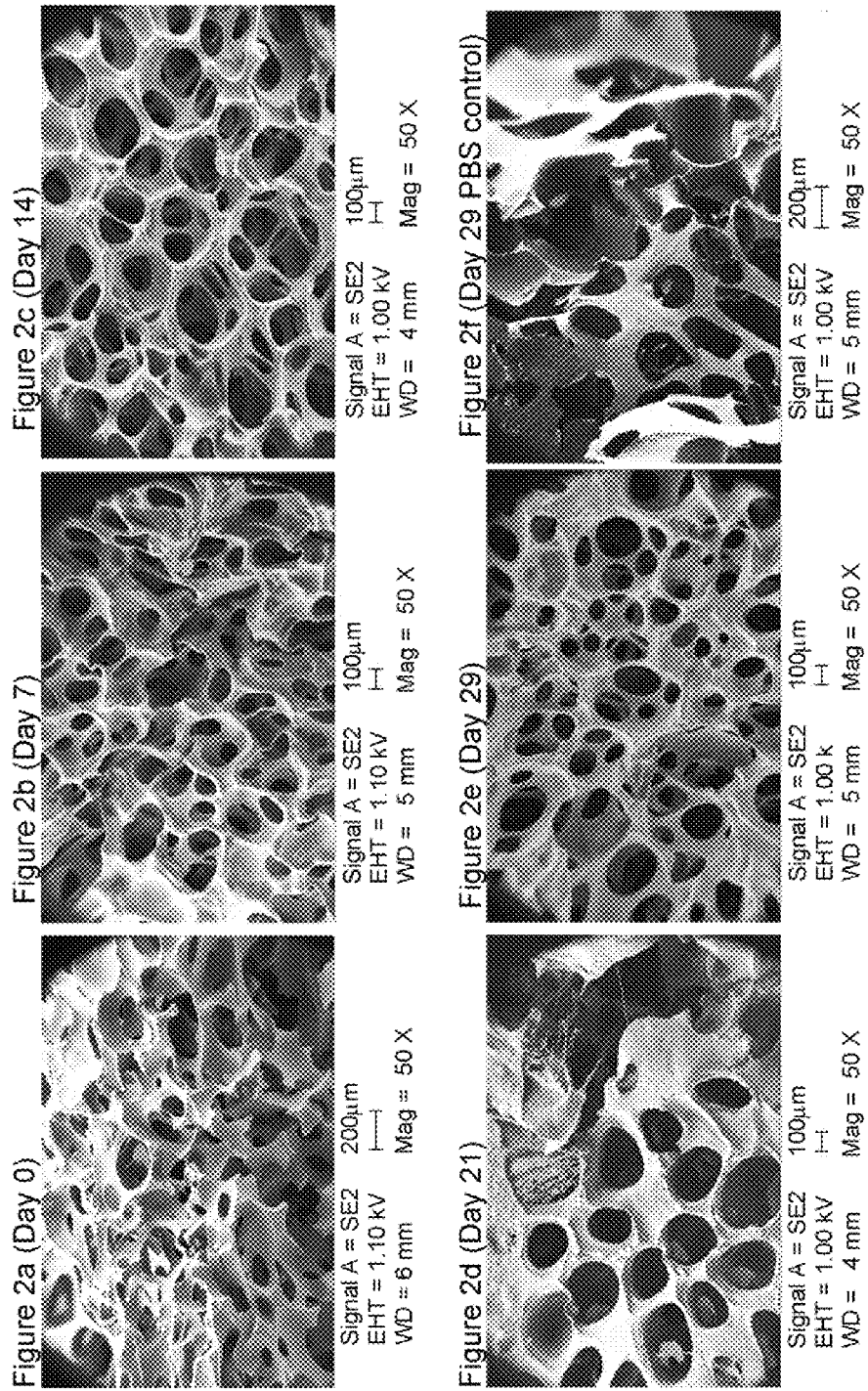
FIGS. 2a-2e are scanning electron micrograph (SEM) images of biodegradable maltodextrin/poly(ethylene glycol) foams at time periods following exposure to amylase; 2f is micrograph (SEM) image of a control.
Figure 3:
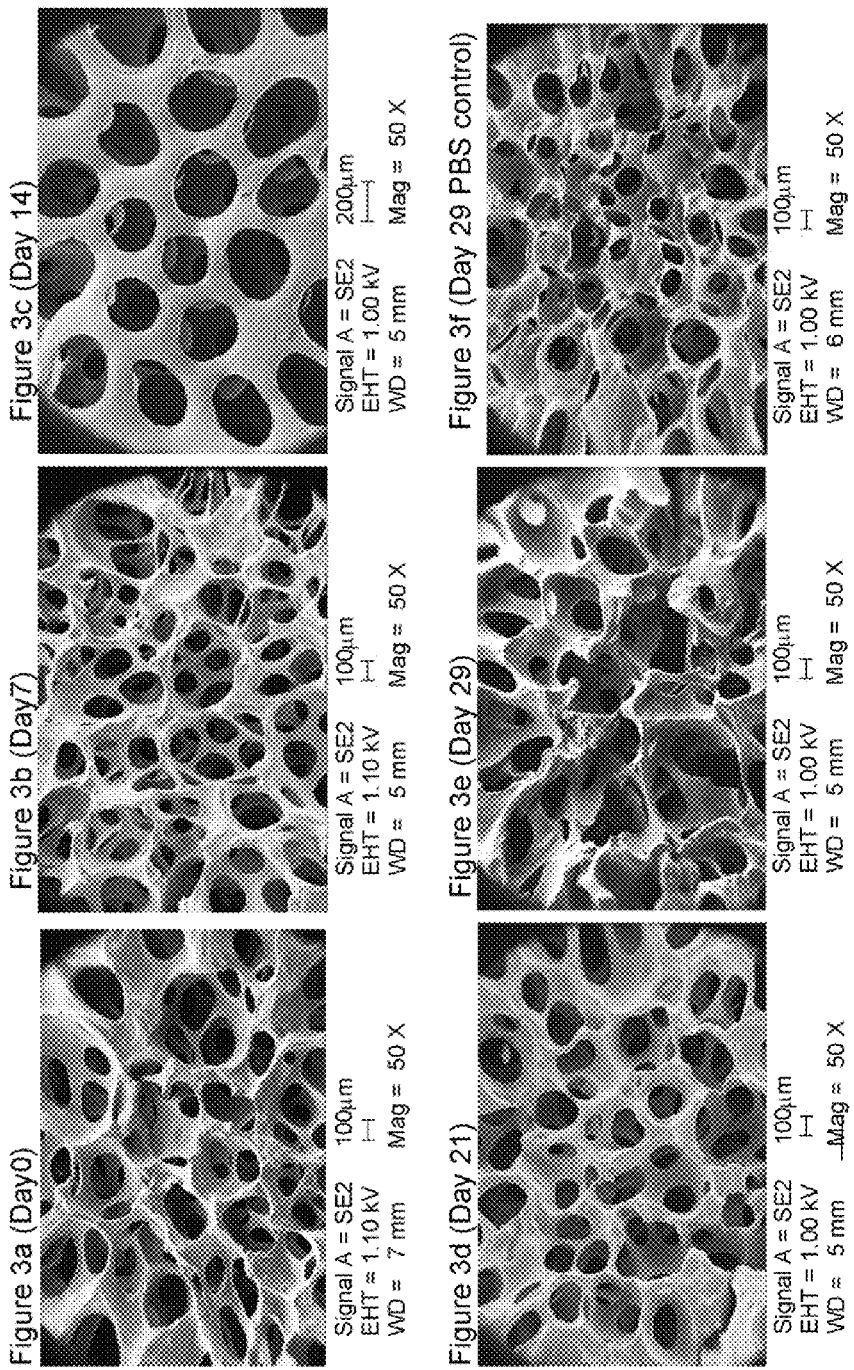
FIGS. 3a-3e are scanning electron micrograph (SEM) images of biodegradable maltodextrin/poly(ethylene glycol) foams at time periods following exposure to amylase; 3f is micrograph (SEM) image of a control.
Figure 4:
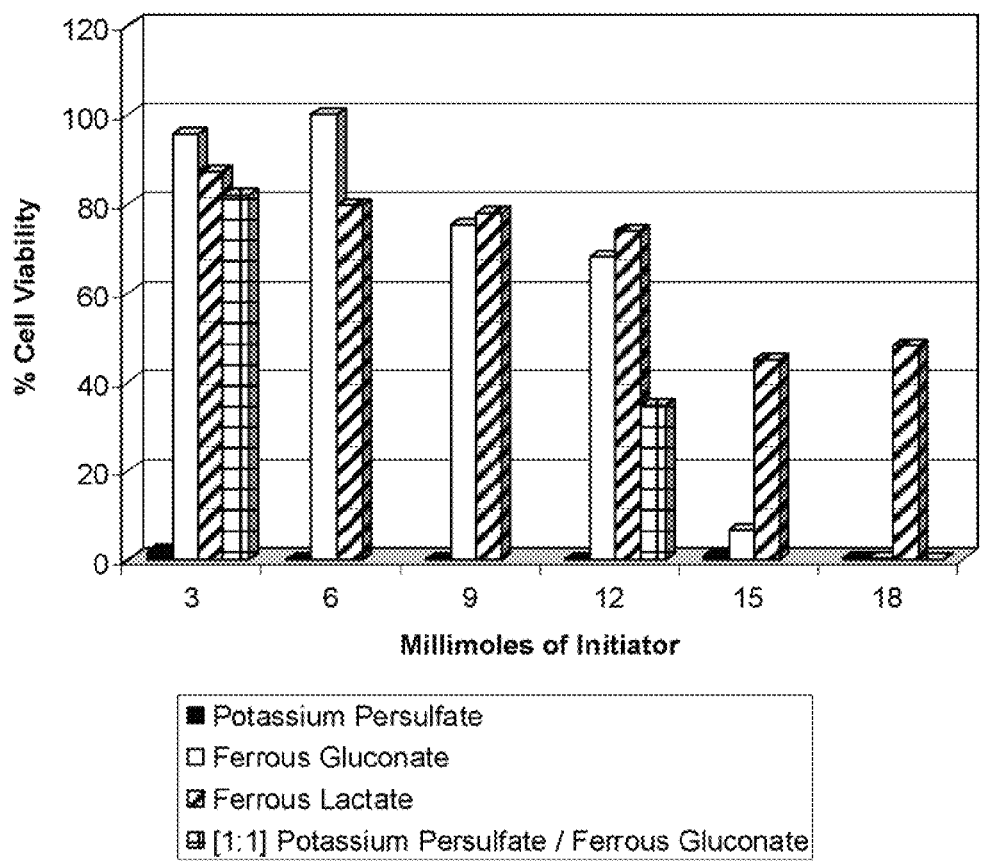
FIG. 4 is a graph representing cell viability in the presence of various polymerization initiator systems, at various concentrations, for the biocompatible foams.
Figure 5:
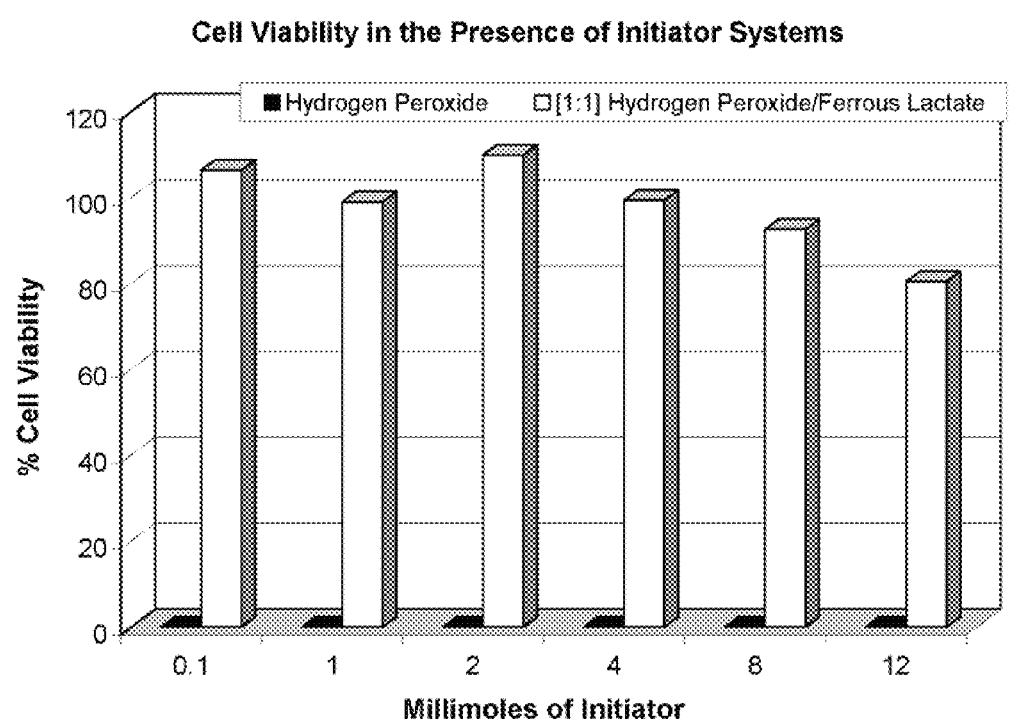
FIG. 5 is a graph representing cell viability in the presence of various polymerization initiator systems, at various concentrations, for the biocompatible foams.

The embodiments of the present invention described below are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The present invention is generally directed at articles, compositions, and methods for the treatment of tissues using biocompatible foams. In some aspects of the invention, the compositions and methods include components that, following application of the composition to the wound site, form a polymerized foam mass (referred to herein as "biocompatible foam" or "polymer foam" or "foam") on the tissue. The foam forming composition applied in situ on a target tissue can be "conformable," meaning that it can create a foam which adapts to the shape of the tissue on which it is applied. The biocompatible foam can also be prepared to have substantial thickness, in addition to a desired width and length. In addition, the thicker biocompatible foams of the invention generally have a uniform porous structure throughout the thickness of the foam. In a uniform porous structure there are little or no collapsed pores and little or no improperly formed portions of the foam (such as non-porous portions). In this regard, the biocompatible foams of the invention can overcome the disadvantages of thinner or flatter foams, which have been described in previous foam forming technologies.

For biodegradable foams of the invention, it is understood that after a period of contact with tissue, which can supply enzymes that break down the polymeric structure of the foam, the structure may change. Therefore, in discussing the properties of the biocompatible foams, reference may be made to their properties (such as porosity, strength, flexibility, etc.) immediately after formation of the foam, unless noted herein. The biostable foams of the invention may also be described in the same manner. The components of the system can be provided in various ways. Typically, the system includes two compositions (or more than two compositions) with components of the system being present in the two compositions. The components are typically present in water-based solutions. To facilitate discussion of the invention, a system having two compositions will be discussed.

In addition to the components of the system, the invention also provides a kit that can include the components of the system and one or more other articles such as devices for mixing solutions in which the components are dissolved. In one mode of practice the system includes two compositions that are mixed and then applied on a tissue site for formation of the polymer foam. The two compositions, prior to mixing, can be referred to as a "first composition" and a "second composition." Although the system can include additional compositions (e.g., a "third composition," etc.) it many modes of practice the foams to be formed by mixing a first composition with the second composition.

The two compositions, when combined, form an "application composition" (also "mixed composition" herein) that includes the polymerizable component, polymerization initiator, and the gas-releasing component. An application composition can be used to form biocompatible foam in situ, or a pre-formed foam. The application composition includes all of the components sufficient for the foam to form when combined. In the application composition, the polymerization initiator and gas producing components are activated. The activated components can be converted to a reaction product. For purposes of discussion, the concentrations of reagents will be discussed in some cases with reference to the first and second compositions (i.e., prior to mixture), and in some cases in the application composition.

Prior to forming the application composition, the combined amount of polymerizable components in the first and second compositions equals the amount of polymerizable components in the application composition. The polymerizable components can be individually present in the first and second compositions in any desired amount, provided the first and second compositions are combined and the total amount of polymerizable material is sufficient to form a polymer foam. In some modes of practice the amount of polymerizable component in the first composition is about the same or the same as in the second compositions.

The biocompatible polymer foams of the invention are formed from macromers. Macromers include "polymerizable group(s)" which generally refers to chemical groups that are polymerizable in the presence of free radicals. A polymerizable group generally includes a carbon-carbon double bond, which can be an ethylenically unsaturated group or a vinyl group. Upon initiation of a polymerization reaction in the application composition, the polymerizable groups, are activated by free radical propagation in the composition, and covalently bonded with other polymerizable groups. As a result of the covalent bonding a crosslinked polymeric matrix is formed. Gas bubbles are generated in the application composition while polymerization of the macromers (which causes polymer matrix formation) is occurring. As a result, a foam is formed, with air pockets (also referred to herein as "cells") partially or completely surrounded by a wall of the crosslinked polymeric matrix.

Exemplary polymerizable groups include acrylate groups, methacrylate groups, ethacrylate groups, 2-phenyl acrylate groups, acrylamide groups, methacrylamide groups, itaconate groups, and styrene groups. In some aspects the macromers of the invention include one or more methacrylate group(s).

Polymerizable groups can be "pendent" from the macromer at more than one location along the polymer backbone. In some cases the polymerizable groups are randomly located along the length of the polymer backbone. Such randomly spacing typically occurs when the macromer is prepared from a polymer having reactive groups along the length of the polymer, and the polymer is reacted with a limited molar quantity of a compound having the polymerizable group. For example, polysaccharides described herein have hydroxyl groups along the length of the polysaccharide, and a portion of these hydroxyl groups are reacted with a compound having a hydroxyl-reactive group and a polymerizable group.

In other cases one or more polymerizable groups are pendent from the macromer at one or more defined locations along the polymer backbone. For example, a polymer used for the synthesis of the macromer can have a reactive group at its terminus, or reactive groups at its termini. Many polymers prepared from monomers with reactive oxygen-containing groups (such as oxides) have hydroxyl-containing terminal ends which can be reacted with a compound having a hydroxyl-reactive group and a polymerizable group to provide the macromer with polymerizable groups at its termini.

The macromers of the invention are based on biocompatible polymers. The term "biocompatible" (which also can be referred to as "tissue compatible") generally refers to the inability of a component, composition, or article to promote a measurably adverse biological response in the body. A biocompatible component, composition, or article can have one or more of the following properties: non-toxic, non-mutagenic, non-allergenic, non-carcinogenic, and/or non-irritating. A biocompatible component, composition, or article, in the least, can be innocuous and tolerated by the body. A biocompatible component, by itself, may also improve one or more functions in the body.

In the context of the present invention, the inventive compositions, methods, and foams can be shown to be biocompatible in one or more ways. For example, the foam-forming compositions can be biocompatible and do not have a component (such as one used to form the foam), or an amount of a component that is that is toxic to cells.

Polymers and macromers of used for making the foams of the invention can be described in terms of molecular weight. "Molecular weight," as used herein, more specifically refers to the "weight average molecular weight" or $M_w$, which is an absolute method of measuring molecular weight and is particularly useful for measuring the molecular weight of a polymer (preparation), such as macromer preparations. Polymer preparations typically include polymers that individually have minor variations in molecular weight. In some cases, the polymers have a relatively higher molecular weight (e.g., versus smaller organic compounds) and such minor variations within the polymer preparation do not affect the overall properties of the polymer preparation (for example, the characteristics of an initiator polymer preparation). The weight average molecular weight ($M_w$) can be defined by the following formula:

$$M_w = \frac{\sum_i N_i M_i^2}{\sum_i N_i M_i}$$

wherein N represents the number of moles of a polymer in the sample with a mass of M, and $\Sigma_i$ is the sum of all $N_i M_i$ (species) in a preparation. The $M_w$ can be measured using common techniques, such as light scattering or ultracentrifugation. Discussion of $M_w$ and other terms used to define the molecular weight of polymer preparations can be found in, for example, Allcock, H. R. and Lampe, F. W., *Contemporary Polymer Chemistry*; pg 271 (1990).

Some aspects of the invention are directed to biocompatible biodegradable foams. In some embodiments, the biodegradable foams are prepared using a poly-α(1→4)glucopyranose-based macromer. A α(1→4)glucopyranose polymer includes repeating glucopyranose monomeric units having α(1→4) linkages and is capable of being enzymatically degraded. Exemplary α(1→4)glucopyranose polymers include maltodextrin, amylose, cyclodextrin, and polyalditol. Maltodextrins generally refer to those polymer preparations having a lower molecular weight than amylose preparations. Cyclodextrins are low molecular weight cyclic α(1→4)glucopyranose polymers.

Maltodextrin is typically generated by hydrolyzing a starch slurry with heat-stable α-amylase at temperatures at 85-90° C. until the desired degree of hydrolysis is reached and then inactivating the α-amylase by a second heat treatment. The maltodextrin can be purified by filtration and then spray dried to a final product. Maltodextrins are typically characterized by their dextrose equivalent (DE) value, which is related to the degree of hydrolysis defined as: DE=MW dextrose/number-averaged MW starch hydrolysate X 100. Generally, maltodextrins are considered to have molecular weights that are less than amylose molecules.

A starch preparation that has been totally hydrolyzed to dextrose (glucose) has a DE of 100, whereas starch has a DE of about zero. A DE of greater than 0 but less than 100 characterizes the mean-average molecular weight of a starch hydrolysate, and maltodextrins are considered to have a DE of less than 20. Maltodextrins of various molecular weights are commercially available.

As used herein, "amylose" or "amylose polymer" refers to a linear polymer having repeating glucopyranose units that are joined by α-1,4 linkages. Some amylose polymers can have a very small amount of branching via α-1,6 linkages (about less than 0.5% of the linkages) but still demonstrate the same physical properties as linear (unbranched) amylose polymers do. Generally amylose polymers derived from plant sources have molecular weights of about 1×10$^6$ Da or less. Amylopectin, comparatively, is a branched polymer having repeating glucopyranose units that are joined by α-1,4 linkages to form linear portions and the linear portions are linked together via α-1,6 linkages. The branch point linkages are generally greater than 1% of the total linkages and typically 4%-5% of the total linkages. Generally amylopectin derived from plant sources have molecular weights of 1×10$^7$ Da or greater.

Exemplary maltodextrin and amylose polymers have molecular weights ranging from about 500 Da, to about 500,000 Da, about 1000 Da, to about 300,000 Da, and about 5000 Da, to about 100,000 Da.

Maltodextrin and amylose polymers of various molecular weights are commercially available from a number of different sources. For example, Glucidex™ 6 (ave. mw ~95,000 Da) and Glucidex™ 2 (ave. mw ~300,000 Da) are available from Rouquette (France); and MALTRIN™ maltodextrins of various molecular weight, including molecular weights from about 12,000 Da to 15,000 Da are available from GPC (Muscatine, Iowa).

The decision of using amylose of a particular size range may depend on factors such as the physical characteristics of the composition (e.g., viscosity), the desired rate of degradation of the foam formed from the polysaccharide, and the presence of other optional components in the foam, such as bioactive agents.

A non-reducing polysaccharide can also be used as degradable polymeric material for forming biodegradable foams. An exemplary non-reducing polysaccharide comprises polyaldi-tol which is available from GPC (Muscatine, Iowa).

Refinement of the molecular weight of a polymer preparation (such as polysaccharide preparations) can be carried out using diafiltration. Diafiltration of polysaccharides such as maltodextrin can be carried out using ultrafiltration membranes with differing pore sizes. As an example, use of one or more cassettes with molecular weight cut-off membranes in the range of about 1K to about 500 K can be used in a diafiltration process to provide polysaccharide preparations with average molecular weights in the range of less than 500 K Da, in the range of about 5 K Da to about 30 K Da, in the range of about 5 K Da to about 30 K Da, in the range of about 10 K Da to about 30 K Da, or in the range of about 1 K Da to about 10 K Da.

Modification of a α(1→4)glucopyranose polymer, such as amylose or maltodextrin, to provide pendent polymerizable groups can be carried out using known techniques. In some modes of preparation, a portion of the hydroxyl groups (which are naturally pendent from α(1→4)glucopyranose polymer) are reacted with a compound having a hydroxyl-reactive group and a polymerizable group. For example, commonly assigned patent application, published as U.S. Pub No. 2007/0065481 (Chudzik et al.) describes modification of α(1→4)glucopyranose polymers to provide pendent acrylate and methacrylate groups.

Modification of α(1→4)glucopyranose polymers with polymerizable groups is explained with reference to the following structure. For example, a portion of the α(1→4)glucopyranose with a pendent polymerizable group can have the following structure:

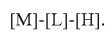

wherein M is a monomeric unit of the α(1→4)glucopyranose polymer, and in the pendent chemical group ([L]-[X]), X is the unsaturated polymerizable group, and L is a chemical group linking the unsaturated polymerizable group to the glucopyranose monomeric unit.

In some cases the chemical linking group L includes a cleavable ester bond. A compounds having a polymerizable group and a hydroxyl reactive groups such as acetal, carboxyl, anhydride, acid halide, and the like, can be used to form a hydrolytically cleavable covalent bond between the polymerizable group and the α(1→4)glucopyranose backbone. For example, the method can provide a α(1→4)glucopyranose polymer with a pendent group having a polymerizable group, the polymerizable group linked to the polysaccharide backbone via a chemical moiety including a cleavable ester bond. In these aspects, the foam will include a polymeric matrix having enzymatically degradable α(1→4) glucopyranose polymer segments and non-enzymatically hydrolytically cleavable chemical linkages between the degradable α(1→4)glucopyranose polymer segments.

Other cleavable chemical linkages that can be used to bond the polymerizable group to the α(1→4)glucopyranose polymer include peroxyester groups, disulfide groups, and hydrazone groups.

In some cases the hydroxyl reactive groups include those such as isocyanate and epoxy. These groups can be used to form a non-cleavable covalent bond between the pendent polymerizable group and the polysaccharide backbone. In these aspects, the foam will include a polymeric matrix having enzymatically degradable α(1→4)glucopyranose polymer segments, but lacking non-enzymatically hydrolytically cleavable chemical linkages.

Exemplary synthetic processes use a α(1→4)glucopyranose polymer (such as maltodextrin) dissolved in dimethylsulfoxide and reacted with a compound having a methacrylate or acrylate group and a hydroxyl reactive group selected from carboxylate, acid chloride, anhydride, azido, and cyanato. Exemplary compounds include (acryloyloxy) propanoic acid, 3-chloro-3-oxopropyl acrylate, 3-azido-3-oxopropyl acrylate, 2-isocyanatoethyl acrylate, methacrylic anhydride, methacrylic acid, and acrylic acid.

The α(1→4)glucopyranose polymer can be prepared with a desired number of pendent polymerizable (e.g., acrylate, methacrylate, etc.) groups suitable for formation of the foams of the present invention. For example, levels of acrylation or methacrylation can be carried out by controlling the amount of reactive compound to the amount of α(1→4)glucopyranose polymer in the reaction mixture. In some aspects, the polymerizable group is present on the α(1→4)glucopyranose macromer at a molar quantity of 0.05 mmol or greater of polymerizable group (such as an acrylate group) per 1 gram of polymer (measurements can also be expressed in μmol/mg). In some aspects the α(1→4)glucopyranose is derivatized with polymerizable groups in amount in the range from about 0.05 mmol to about 2 mmol of polymerizable group (such as an acrylate group) per 1 gram of macromer. In some favored modes of practice, the biocompatible biodegradable forms are formed using a α(1→4)glucopyranose polymer having a level of polymerizable group derivatization in the range of about 0.05 mmol to about 0.4 mmol polymerizable group (e.g., acrylate, methacrylate) per gram of polysaccharide, or more specifically about 0.1 mmol/gram to about 0.35 mmol/gram.

The α(1→4)glucopyranose polymer may also include one or more other chemical modifications that are different than those provided by the polymerizable group. The α(1→4) glucopyranose polymer may be modified in a way to change its chemical properties. Generally, if such modifications are made they do not adversely impact the ability of the α(1→4)glucopyranose to be useful in forming a biodegradable foam.

For example, the α(1→4)glucopyranose polymer may be derivatized with hydrophobic groups. This may be useful in reducing the hydrophilic character of the foam and in turn could decrease the rate that the foam degrades when in contact with tissue or body fluid. Hydrophobic groups can be added to the polysaccharide in a manner similar to that of adding polymerizable groups. For example a compound having a hydrophobic group, such as an alkyl chain of a fatty acid, and a group reactive with a hydroxyl group of the polysaccharide is used to derivatize the α(1→4)glucopyranose polymer. Exemplary compounds and methods for adding hydrophobic groups are described in U.S. Pub No. 2007/0065481 (supra), see Example 46. If hydrophobic groups are added, the derivatized α(1→4)glucopyranose polymer desirably remains soluble in a biocompatible application composition and is able to be polymerized into a biocompatible biodegradable foam.

The α(1→4)glucopyranose-based macromer can be used at a final concentration in the application composition sufficient to form a foam when the polymerization initiator and gas generation components are activated. As a general matter, higher concentrations of α(1→4)glucopyranose-based macromer can be used to form foams that are denser, harder, and less flexible. In many modes of practice the α(1→4)glucopyranose-based macromer is present in the application composition at a concentration in the range of 200 mg/mL to 1000 mg/mL, about 400 mg/mL to about 700 mg/mL, or about 500 mg/mL to about 600 mg/mL. If one or more other macromers are present in the application composition in addition to the α(1→4)glucopyranose-based macromer can be present in a lesser amount, such as in the range of about 100 mg/mL to about 500 mg/mL, about 200 mg/mL to about 400 mg/mL, or about 200 mg/mL to about 350 mg/mL.

In some aspects the biocompatible biodegradable foam is formed from at least a α(1→4)glucopyranose-based macromer and another biocompatible polymer comprising one or more pendent polymerizable groups. For purposes of discussion, this additional macromer is referred to herein as the "second macromer" of the biocompatible biodegradable foam. In many aspects the second macromer is formed from a biostable hydrophilic biocompatible polymer. A biostable biocompatible polymer refers to one that does not break down into monomeric units when placed in contact with tissue according to the methods of the invention, but yet is biocompatible and does not cause adverse affects in the body. Such a biostable biocompatible polymer may be eliminated from the body through urination or excretion.

A foam that is formed from the α(1→4)glucopyranose-based macromer and second macromer can form the solid component of the foam which is a polymeric matrix. The polymeric matrix can therefore have enzymatically degradable and non-degradable polymeric segments that are crosslinked via polymerized groups. Optionally, depending on the linkages between the polymeric portions and the polymerized groups, the polymeric matrix of the foam can also be non-enzymatically hydrolytically degradable, in addition to being enzymatically degradable.

After the biocompatible biodegradable foam is formed or placed at a target sited on the body, it degrades at a certain rate. The degradation can be caused entirely or partially by amylases causing the enzymatic degradation of the poly α(1→4)glucopyranose segments. Depending on the linkage of the acrylate or methacrylate groups, non-enzymatic hydrolysis of unsaturated esters can also occur, further promoting the degradation of the foam. Degradation of the poly α(1→4)glucopyranose also results in liberation of the polymeric segments formed from the second macromers, which can be eliminated from the body.

Exemplary polymers that that can be used to form the second macromer can be based on one or more of the following hydrophilic biocompatible polymers: poly(vinylpyrrolidone) (PVP), poly(ethylene oxide) (PEO), poly(ethyloxazoline), poly(propylene oxide) (PPO), poly(meth)acrylamide (PAA) and poly(meth)acrylic acid, poly(ethylene glycol) (PEG) (see, for example, U.S. Pat. Nos. 5,410,016, 5,626,863, 5,252,714, 5,739,208 and 5,672,662) PEG-PPO (copolymers of polyethylene glycol and polypropylene oxide), hydrophilic segmented urethanes (see, for example, U.S. Pat. Nos. 5,100,992 and 6,784,273), and polyvinyl alcohol (see, for example, U.S. Pat. Nos. 6,676,971 and 6,710,126).

In some aspects, the second macromer used to form the biocompatible foam has a molecular weight in the range of 100 Da to 10,000 Da, or about 200 Da to about 10,000 Da.

In some aspects, the second macromer is formed from an oxyalkylene polymer. An oxyalkylene polymer refers to a polymer that includes repeating units of the formula component —($R^1$—O)—, where $R^1$ is a substituted or unsubstituted divalent hydrocarbon group having 1 to about 8 carbon atoms. In some modes of practice, $R^1$ is a hydrocarbon group having 2, 3, or 4 carbon atoms. The oxyalkylene polymer can be formed from monomeric units in which $R^1$ is different. For example, the oxyalkylene polymer can be formed from a combination of monomeric units wherein $R^1$ individually, has 2 carbon atoms and 3 carbon atoms.

The oxyalkylene polymer can also be formed from monomeric units other than —($R^1$—O)—. In some modes of practice the monomeric units of —($R^1$—O)— in the oxyalkylene polymer account for 50 weight percent of the polymer or greater.

The oxyalkylene polymer can be an alkylene oxide polymer such as an ethylene glycol or propylene glycol polymer (e.g., poly(ethylene glycol) and poly(propylene glycol), respectively). In some cases an ethylene glycol polymer or oligomer having the structure HO—($CH_2$—$CH_2$—O)$_n$—H is used to form the second macromer for the biodegradable foam. As an example, the value of n ranges from about 3 to about 150 and the number average molecular weight (Mn) of the poly(ethylene glycol) ranges from about 100 Da to about 5000 Da, more typically ranging from about 200 Da to about 3500 Da, from about 250 Da to about 2000 Da, from about 250 Da to about 1500 Da, or about 400 Da to about 1000 Da.

In some aspects the biocompatible biodegradable foam is formed from at least a α(1→4)glucopyranose-based macromer and linear oxyalkylene polymer. Linear oxyalkylene polymers are described herein. In some aspects the biocompatible biodegradable foam is formed from at least a α(1→4) glucopyranose-based macromer and a branched compound containing oxyalkylene polymeric portion. Branched compounds containing oxyalkylene polymeric portions are also described herein.

An oxyalkylene polymer can be effectively derivatized to add polymerizable groups to produce oxyalkylene based macromers. Polymerizable groups such as glycidyl acrylate, glycidyl methacrylate, acrylic or methacrylic acid can be reacted with the terminal hydroxyl groups of these polymers to provide terminal polymerizable groups. Acrylate and methacrylate-containing poly(ethylene glycols) or poly(propylene glycols) are also commercially available (for example from Aldrich Chemicals). Exemplary levels of derivation are in the range of about 0.001 mol to about 0.01 mol polymerizable group per gram of oxyalkylene polymer.

Some specific examples of alkylene oxide polymer-based macromers include, poly(propylene glycol)$_{540}$-diacrylate, poly(propylene glycol)$_{475}$-dimethacrylate, poly(propylene glycol)$_{900}$-diacrylate, include poly(ethylene glycol)$_{250}$-diacrylate, poly(ethylene glycol)$_{575}$-diacrylate, poly(ethylene glycol)$_{550}$-dimethacrylate, poly(ethylene glycol)$_{750}$-dimethacrylate, poly(ethylene glycol)$_{700}$-diacrylate, and poly(ethylene glycol)$_{1000}$-diacrylate.

In other modes of practice, the second macromer used to form the biodegradable foam comprises a non-enzymatic hydrolytically degradable polymeric portion. Exemplary polymers that are hydrolytically degradable and that can be used to form the second macromer can be based polyesters such as poly(lactic acid) (poly(lactide)), poly(glycolic acid) (poly(glycolide)), poly(lactide-co-glycolide), poly(dioxanone); polylactones such as poly(caprolactone) and poly(valerolactone), and copolymers such as poly(glycolide-co-polydioxanone), poly(glycolide-co-trimethylene carbonate), and poly(glycolide-co-caprolactone).

Polyesters such as poly(lactic acid) have terminal hydroxyl groups and can be acrylated through the use of acryloyl chloride.

Biodegradable polyetherester copolymers can also be used to form the second macromer. Generally speaking, polyetherester copolymers are amphiphilic block copolymers that include hydrophilic (for example, a polyalkylene glycol, such as polyethylene glycol (PEG)) and hydrophobic blocks (for example, polyethylene terephthalate). Examples of block copolymers include poly(ethylene glycol)-based and poly (butylene terephthalate)-based blocks (PEG/PBT polymer). Examples of these types of multiblock copolymers are described in, for example, U.S. Pat. No. 5,980,948. PEG/PBT polymers are commercially available from Octoplus BV (Leiden, Netherlands), under the trade designation PolyActive.

Other PEG-containing block copolymers, such as those including one or more polymeric blocks selected from poly (hydroxybutyrate) (PHB), poly(oxyethylene) (POE), poly (caprolactone) (PCL), and poly(lactide) (PLA) are available from Advanced Polymer Materials, Inc. (Lachine, QC, Canada).

The second macromer can be used in combination with the α(1→4)glucopyranose-based macromer at a final concentration in the application composition sufficient to form a foam when the polymerization initiator and gas generation components are activated. In many modes of practice the second macromer, such as an alkylene oxide polymer-based macromer, is present in the application composition at a concentration in the range of about 100 mg/mL to about 500 mg/mL, about 100 mg/mL to about 400 mg/mL, about 100 mg/mL to about 350 mg/mL, or about 150 mg/mL to about 300 mg/mL. Prior to combining with the composition including the α(1→4)glucopyranose-based macromer, the second macromer can be in a composition (e.g., a "second composition") in an amount in the range that is double these concentrations.

The amounts of macromer materials in the application composition can also be described in terms of the weight ratio between the amounts of the α(1→4)glucopyranose-based macromer and second macromer (such as an alkylene oxide polymer-based macromer). In some modes of practice, the ratio between the α(1→4)glucopyranose-based macromer and second macromer is in the range of about 1:1 to about 3:1, about 1:1 to about 2:1, and more specifically in the range of about 1.1:1 to about 1.5:1. In one exemplary aspect the ratio is about 1.3:1.

Other aspects of the invention are directed to biocompatible biostable foams. In some embodiments, the biostable foams are prepared using a combination of (at least) a first biostable macromer and a second biostable macromer. The first biostable macromer comprises a covalently crosslinkable branched hydrophilic polymer comprising pendent polymerizable group(s). The second biostable macromer is a covalently crosslinkable linear hydrophilic polymer comprising pendent polymerizable group(s). In favored aspects, the first biostable macromer comprises a covalently crosslinkable branched alkylene oxide polymer comprising pendent polymerizable group(s).

A biostable foam that is created from the branched alkylene oxide-based macromer and linear hydrophilic macromer can form the solid component of the foam. The solid component comprises a polymeric matrix with non-degradable polymeric segments that are crosslinked via reacted polymerizable groups.

The first macromer comprises a branched (non-linear) compound comprising three or more hydrophilic polymeric portions and pendent reactive groups. A "non-linear" or "branched" compound having polymeric portions refers to those having a structure different than a linear polymer (which is a polymer in which the molecules form long chains without branches or cross-linked structures). Such a compound can have multiple polymeric "arms" which are attached to a common linking portion of the compound. Non-linear or branched compounds are exemplified by, but not limited to, those having the following general structures:

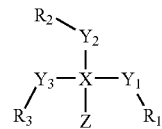

Formula I wherein X is a linking atom, such as one selected from C or S, or a linking structure, such a homo- or heterocyclic ring; to $Y_1$ to $Y_3$ are bridging groups, which can independently be, for example, —$C_n$—O— wherein n is 0 or an integer of 1 or greater; $R_1$ to $R_3$ are independently hydrophilic polymeric portions, which can be the same or different, and have one or more pendent polymerizable groups; and Z is a non-polymeric group, such as a short chain alkyl group.

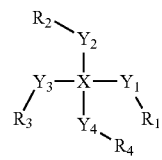

Formula II wherein X is a linking atom, such as one selected from C or S, or a linking structure, such a homo- or heterocyclic ring; to $Y_1$ to $Y_4$ are bridging groups, which can individually be, for example, —$C_n$—O—, wherein n is 0 or an integer of 1 or greater; and $R_1$ to $R_4$ independently hydrophilic polymeric portions, which can be the same or different, and have one or more pendent polymerizable groups.

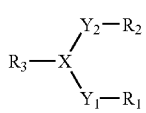

Formula III wherein X is a linking atom or group, such as one selected from N, C—H, or S—H, or a linking structure, such a homo- or heterocyclic ring; to $Y_1$ and $Y_2$ are bridging groups, which can individually be, for example, —$C_n$—O—, wherein n is 0 or an integer of 1 or greater; and $R_1$ to $R_3$ independently hydrophilic polymeric portions, which can be the same or different, and have one or more pendent polymerizable groups.

The branched structures also include polymerizable groups. The polymerizable groups can be pendent from the polymeric portions of the compound. In many aspects the branched compounds have one polymerizable group per polymeric branched portion (R) of the compound. In these aspects, the compounds of Formula I and III have three polymerizable groups, and the compounds of Formula II have two polymerizable groups. In many aspects the polymerizable groups are located at the termini of the polymeric portions R.

A branched macromer can be prepared from a polyol, such as a low molecular weight polyol (for example, a polyol having a molecular weight of 200 Da or less). In some aspects the branched macromer can be derived from a triol, a tetraol, or other multifunctional alcohol. Exemplary polyol derivatives include derivatives of pentaerythritol, trimethylolpropane, and glycerol.

The polymeric portions of the branched macromer can be selected from PVP, PEO, poly(ethyloxazoline), PPO, PAA and poly(meth)acylic acid, PEG, and PEG-PPO, hydrophilic segmented urethanes, and polyvinyl alcohol, such as those described herein.

In some aspects, the branched macromer comprises one or more polymeric portions that is or are an oxyalkylene polymer, such as an ethylene glycol polymer.

For example, the preparation of a PEG-triacrylate macromer (trimethylolpropane ethoxylate (20/3 EO/OH) triacrylate macromer), which can be used as the branched macromer, is described in Example 5 of commonly assigned U.S. Patent Application Publication No. 2004/0202774A1 (Chudzik, et al.).

In some aspects, the branched macromer has a molecular weight in the range of about 300 Da to about 20 kDa, or more specifically in the range of about 500 Da to about 2500 Da.

The second macromer (linear macromer) is based on a linear hydrophilic polymer. Exemplary polymers that that can be used to form the linear macromer can be based on one or more of the following polymers: poly(vinylpyrrolidone) (PVP), poly(ethylene oxide) (PEO), poly(ethyloxazoline), poly(propylene oxide) (PPO), poly(meth)acrylamide (PAA) and poly(meth)acylic acid, poly(ethylene glycol) (PEG) (see, for example, U.S. Pat. Nos. 5,410,016, 5,626,863, 5,252,714, 5,739,208 and 5,672,662) PEG-PPO (copolymers of polyethylene glycol and polypropylene oxide), hydrophilic segmented urethanes (see, for example, U.S. Pat. Nos. 5,100,992 and 6,784,273), and polyvinyl alcohol (see, for example, U.S. Pat. Nos. 6,676,971 and 6,710,126).

In some aspects, the linear macromer has a molecular weight in the range of 100 Da to 5000 Da.

In some aspects, macromers used to form the biostable foam are formed from oxyalkylene polymers as described herein. Oxyalkylene polymers used to form macromers for the biostable foam can include repeating units of the formula component —($R^1$—O)—, where $R^1$ is a substituted or unsubstituted divalent hydrocarbon group having 1 to about 8 carbon atoms. In some modes of practice, $R^1$ is a hydrocarbon group having 2, 3, or 4 carbon atoms. Oxyalkylene polymers can be formed from monomeric units in which $R^1$ is different. For example, the oxyalkylene polymer can be formed from a combination of monomeric units wherein $R^1$ individually, has 2 carbon atoms and 3 carbon atoms.

The oxyalkylene polymer can also be formed from monomeric units other than —($R^1$—O)—. In some modes of practice the monomeric units of —($R^1$—O)— in the oxyalkylene polymer account for 50 weight percent of the polymer or greater.

Macromers used to form the biostable foam can be alkylene oxide polymers such as an ethylene glycol or propylene glycol polymer (e.g., poly(ethylene glycol) and poly(propylene glycol), respectively). In some cases an ethylene glycol polymer or oligomer having the structure HO—($CH_2$—$CH_2$—O)$_n$—H is used to form the second macromer for the biodegradable foam. As an example, the value of n ranges from about 3 to about 150 and the number average molecular weight (Mn) of the poly(ethylene glycol) ranges from about 100 Da to about 5000 Da, more typically ranging from about 200 Da to about 3500 Da, from about 250 Da to about 2000 Da, from about 250 Da to about 1500 Da, or about 400 Da to about 1000 Da.

Some specific examples of alkylene oxide polymer-based macromers that can be used to form biostable foams include, poly(propylene glycol)$_{540}$-diacrylate, poly(propylene glycol)$_{475}$-dimethacrylate, poly(propylene glycol)$_{900}$-diacrylate, include poly(ethylene glycol)$_{250}$-diacrylate, poly(ethylene glycol)$_{575}$-diacrylate, poly(ethylene glycol)$_{550}$-dimethacrylate, poly(ethylene glycol)$_{750}$-dimethacrylate, poly(ethylene glycol)$_{700}$-diacrylate, poly(ethylene glycol)$_{1000}$-diacrylate.

The polymerization initiator can be any suitable component (or combinations of components) that drive free radical polymerization of the polymerizable material to form the polymer foam. Many polymerization initiators are known in the art and are commercially available and can be used in situ to form the polymer foam without causing an adverse affect of the wound site.

In some modes of practice, the polymerization initiator includes members of a "redox pair" (an oxidizing agent/reducing agent pair). The free radicals are generated by reaction of the initiator, i.e., an oxidant, with the activator or catalyst, i.e., a reductant. Compounds that represent members of a redox pair would be included in a system having two (or more) compositions, in view of the reactive nature of the first and second members of the redox pair. In other words, first and second members of the redox pair are typically held in separate compositions until the time that the application composition is made (which activates the redox components), and which promotes foam formation. In one aspect, the systems of the invention include a first solution with one member of a redox pair and second solution with the other member of a redox pair.

The oxidizing agent/initiator can be selected from inorganic or organic oxidizing agents, including enzymes. The reducing agent can be selected from inorganic or organic reducing agents, including enzymes. Exemplary oxidizing agents include peroxides, including hydrogen peroxide, metal oxides, and oxidases, such as glucose oxidase.

Exemplary activators include salts and derivatives of electropositive elemental metals such as Li, Na, Mg, Fe, Zn, Al, and reductases. Exemplary salts of these electropositive elemental metals includes gluconates, ascorbates, acetylacetonates, fumarates, and lactates.

According to experimental studies associated with the invention, it has been found that $Fe^{2+}$-based activators provide advantages over other types of metal based activators. Given this, the use of a $Fe^{2+}$-based initiator system can improve properties of the biocompatible foams of the invention (as well as the compositions and methods used to form the foams).

According to other experimental studies associated with the invention, it has been found that it has found that certain $Fe^{2+}$-based activators performed exceptionally well in driving polymerization of the macromer materials during the foaming process, which resulted in the rapid set-up of biocompatible foams with desirable properties.

Given these findings, in some embodiments of the invention, the compositions or methods comprises an activator selected from the group consisting of $Fe^{2+}$-gluconate, $Fe^{2+}$-ascorbate, $Fe^{2+}$-acetylacetonate, and $Fe^{2+}$-lactate. $Fe^{2+}$-gluconate or $Fe^{2+}$-lactate are advantageously used in the compositions and methods of the invention.

According to other experimental studies associated with the invention, it has been found that peroxide-based activators performed surprisingly well in cell viability assays. When used in along with a suitable activator, cell viability, even using a higher concentrations of hydrogen peroxide (such as about 12 mmol) remained very good.

Given these findings, in some embodiments of the invention, the compositions or methods comprise a peroxide-based initiator. Peroxide-based initiators include, but are not limited to, diacyl peroxides, peroxyesters, dialkyl peroxides, peroxyketals, ketone peroxides, hydroperoxides. In some aspects the initiator is hydrogen peroxide ($H_2O_2$). Diacyl peroxides include, but are not limited to, benzoyl peroxide, 2,4-dichlorobenzoyl peroxide, m-toluoyl peroxide, lauroyl peroxide, and dibenzoyl peroxide. Hydroperoxides include, but are not limited to, t-butyl hydroperoxide, cumene hydroperoxide, and p-diisopropylbenzene peroxide.

In many modes of practice the first and second member of the redox pair are used at about the same, or the same concentration. For example, prior to combining to form an application composition the concentration of the first and second member of the redox pair in the pre-compositions (e.g., "first" or "second" composition) can be, individually, about 2.0 mM or greater, about 2.5 mM or greater, or about 5 mM or greater. Exemplary ranges are from about 2.0 mM to about 25 mM, or about 2.5 mM to about 15 mM.

The gas-generating component can provide any suitable gas for expansion of the solid component of the foam which is produced as the macromers polymerize in the application composition.

In one mode of practice, the gas-generating component includes two compounds that are separated into two compositions (e.g., a first composition and a second composition) of the system. One compound is the gas-generating compound and the other is an activator that is reactive with the gas-generating compound to cause formation of the gas. An exemplary pair representing the gas-generating component is a carbonate-containing compound, such as a bicarbonate salt (e.g., potassium or sodium bicarbonate) and a biocompatible acid, for example, citric acid, etc.

The gas-generating component can be used in an amount sufficient for formation of the polymer foam on the wound site. This amount of gas-generating component present in the application composition can be chosen based on the amount of polymerizable material present in the application composition. For example, prior to combining to form an application composition the concentration of the acid and bicarbonate salt in the pre-compositions (e.g., "first" or "second" composition) can be, individually, about 40 mg/mL or greater, such as in the range of about 40 mg/mL to about 160 mg/mL, or more specifically in the range of about 80 mg/mL to about 120 mg/mL. In one exemplary mode of practice the system provides a first (pre-mixed) composition including a bicarbonate salt at a concentration of about 100 mg/mL, and second (pre-mixed) composition including an acid at a concentration of about 100 mg/mL.

In some modes, the ratio (by weight) between the amount of the gas-generating component and the amount of polymerizable material in the system is about 1:20 or greater, such as in the range of about 1:20 to about 1:1, or about 1:12 to about 1:5. In one exemplary mode of practice, the ratio between the amount of the gas-generating component and the amount of polymerizable material in the system is about 1:9.

In some modes of practice, the biocompatible foam can be formed using a surfactant, or a combination of surfactants. A surfactant can improve formation of the foam arrangement by promoting the creation of well-structured air pockets from the emerging air bubbles as the macromers polymerize. Surfactants can also increase the porosity of the foam. As such, the surfactant can prevent the pores from collapsing upon themselves during foam formation.

Various biocompatible surfactants are know in the art and/or are commercially available and that can be used in conjunction with the methods described herein to form biocompatible foams. Biocompatible surfactants include phosphatidyl choline (lecithin) alkyl(poly)glycosides, sodium bis(2-ethylhexyl) sulfosuccinate (AOT), sodium dodecyl sulphate (SDS), polyoxyethylene sorbitan n-acyl esters (Tweens), and poloxamers (Pluronics).

In one mode of practice it has been found desirable to use a poloxamer as a surfactant for forming biocompatible foams. Based on experimental studies associated with the invention it has been shown that poloxamers can be included in the foam forming compositions and promote the formation foam structures with highly desirable properties. While not intending to be bound by theory, it is thought that foams formed from a macromer and a surfactant having similar chemical features (e.g., the presence of a poly(ethylene oxide) portion in both the macromer and the surfactant) provide excellent foam structures.

Poloxamers include a central hydrophobic poly(propylene oxide) portion with flanking hydrophilic poly(ethylene oxide) portions. Poloxamers, many of which are commercially available under the trade name Pluronics™ (BASF Corp.) include nonionic triblock copolymers of PEO-PPO-PEO having variations in the PPO core and the PEO content. Poloxamers are available in liquid, paste, and flake form. In some modes of practice poloxamer in the form of a wax. One exemplary poloxamer is Pluronic™ 25R4, which has a hydrophile-lipophile balance in the range of 7-12. Another exemplary poloxamer is Pluronic™ 31R1. In some modes of practice a biodegradable foam is prepared using PEG-monomethacrylate and a poloxamer.

In some aspects, a surfactant(s) is present in the application composition in an amount in the range of about 0.5 mg/mL to about 15 mg/mL, about 1 mg/mL to about 10 mg/mL, or about 3.5 mg/mL.

In some modes of practice, the biocompatible foam is formed using with the foam forming components in an emulsion. In other words, when the foam-forming components are mixed, the composition including the mixed components is in the form of an emulsion, which produces gas bubbles and polymerizes to foam.

An emulsion can be formed when the mixed composition includes polymeric components that are not completely miscible in the same liquid. Examples of second macromers that may not be miscible with poly α(1→4)glucopyranose-based macromers include poly-glycolide based macromers. A first compositions can be prepared having the α(1→4)glucopyranose-based macromer, and a second composition can be prepared having the poly-glycolide based macromers dissolved in a solvent that is different than the first composition. One or both of the compositions may include a component which helps promote and/or stabilize emulsion formation. The compositions are mixed together and an emulsion is formed, with polymerization of the macromer materials and gas generation.

In situ foam formation from an emulsified composition can includes liquids such as water, dimethylsulfoxide (DMSO), alcohols such as ethanol and isopropanol, and fatty acid alcohols. Non-water liquids can be used at low concentrations in the to enhance emulsion formation and provide a biocompatible composition.

Pre-formed foams can be formed from emulsions prepared using a wider selection of solvents. These solvents can be removed from the pre-formed foams prior to introduction of the foam in the body.

The foam-forming composition can also include one or more biologically active agents that can improve the process of treating the tissue site on which the foam is formed or applied.

Bioactive agents can be released from the foams of the invention in one or more ways. In some aspects, a biodegradable foam can include a bioactive agent that is entrapped in the crosslinked polymeric matrix of the foam structure. As the polymeric material of the matrix is degraded after it has been placed in contact with tissue, the bioactive agent is released from the matrix and becomes available to the tissue and/or fluid that the foam is in contact with. In many aspects the entrapped bioactive agent is a macromolecule, or the bioactive agent is in a particulate form. The particulate can be held within the crosslinked matrix of polymeric material As another example, the bioactive agent elutes out of the crosslinked polymeric matrix of the foam structure. Elution of the bioactive agent can be caused by the hydrophilicity of the polymeric materials of the foam, which can drive water into the matrix and cause an increase in the osmotic pressure in the matrix. As a result, the permeability of the coating for the bioactive agent is increased, and results in the elution of the bioactive agent from the foam.

Alternatively, the bioactive agent is coupled to the one or more matrix materials of the foam. In these cases it can be desirable for the foam to provide bioactivity without the molecule that is responsible for the bioactivity being released from the foam materials. For example, the foam is prepared with a bioactive agent that can be covalently coupled to the polymeric material that is used to make the foam. As an example, covalent coupling can be carried out by derivatizing a bioactive agent with a polymerizable group and then copolymerizing the matrix forming material with the bioactive agent. Another method involves derivatizing the bioactive agent with a photoreactive group and then activating the matrix in the presence of the photoreactive group to couple the bioactive agent to the matrix material of the foam. Photoderivatized bioactive agents are known in the art and described in, for example, U.S. Pat. No. 4,722,906 (Guire et al.). A third method includes the covalent attachment of the bioactive molecule to the polymerizable moieties which are then subsequently crosslinked into the foam.

A partial list of bioactive agents is provided below. A comprehensive listing of bioactive agents, in addition to information of the water solubility of the bioactive agents, can be found in *The Merck Index*, Thirteenth Edition, Merck & Co. (2001).

The foams prepared according to the invention can be used to release bioactive agents falling within one or more of the following classes include, but are not limited to: ACE inhibitors, actin inhibitors, analgesics, anesthetics, anti-hypertensives, anti polymerases, antisecretory agents, anti-AIDS substances, anti-apoptotic, antibiotics, anti-cancer substances, anti-cholinergics, anti-coagulants, anti-convulsants, anti-depressants, anti-emetics, antifungals, anti-glaucoma solutes, antihistamines, antihypertensive agents, anti-inflammatory agents (such as NSAIDs), anti metabolites, antimitotics, anti-oxidizing agents, anti-parasite and/or anti-Parkinson substances, antiproliferatives (including antiangiogenesis agents), anti-protozoal solutes, anti-psychotic substances, anti-pyretics, antiseptics, anti-spasmodics, antiviral agents, calcium channel blockers, cell cycle proteins, cell response modifiers, chelators, chemotherapeutic agents, dopamine agonists, extracellular matrix components, fibrinolytic agents, free radical scavengers, growth factors, growth hormone antagonists, homing factors, hypnotics, immunosuppressive agents, immunotoxins, inhibitors of surface glycoprotein receptors, microtubule inhibitors, miotics, muscle contractants, muscle relaxants, neurotoxins, neurotransmitters, polynucleotides and derivatives thereof, opioids, photodynamic therapy agents, prostaglandins, remodeling inhibitors, statins, steroids, thrombolytic agents, tranquilizers, vasodilators, and vasospasm inhibitors.

In some aspects of the invention, the foam includes a bioactive agent that is a macromolecule. Exemplary macromolecules can be selected from the group consisting of polynucleotides, polysaccharides, and polypeptides. In some aspects the bioactive agent has a molecular weight of about 1000 Da or greater.

One class of bioactive agents that can be released from the foam includes polynucleotides. As used herein "polynucleotides" includes polymers of two or more monomeric nucleotides. Nucleotides can be selected from naturally occurring nucleotides as found in DNA (adenine, thymine, guanine, and cytosine-based deoxyribonucleotides) and RNA (adenine, uracil, guanine, and cytosine-based ribonucleotides), as well as non-natural or synthetic nucleotides.

Types of polynucleotides that can be released from the matrix include plasmids, phages, cosmids, episomes, integratable DNA fragments, antisense oligonucleotides, antisense DNA and RNA, aptamers, modified DNA and RNA, iRNA (immune ribonucleic acid), ribozymes, siRNA (small interfering RNA), miRNA (micro RNA), locked nucleic acids and shRNA (short hairpin RNA). Antisense oligonucleotides hybridize to a specific complementary portion of a mRNA. Hybridization with the antisense molecule results in the degradation of the RNA duplex by RNAse H and results in decreased production of the protein encoded by the targeted mRNA. RNA interference (RNAi) refers to target-specific gene silencing, and can be performed using via short interfering RNA (siRNA). Double-stranded siRNA introduced into a cell is recognized by the RNA induced silencing complex, which separates the strands, promotes hybridization of the antisense strand to the target mRNA, and then cleaves the target strand. Accordingly, siRNAs can reduce expression of select proteins. Some enzymatic RNA molecules, known as ribozymes, can catalyze the cleavage and destruction of target RNA molecules.

In aspects, the foams include an antibiotic. Exemplary antibiotics include topical antibiotics such as bacitracin, mupirocin (Bactroban), and retapamulin (Altabax). Other examples of antibiotics include penicillin, tetracycline, chloramphenicol, minocycline, doxycycline, vancomycin, kanamycin, neomycin, gentamycin, erythromycin, cephalosporins, geldanamycin, and analogs thereof.

In aspects, the foams include a polypeptide which promotes tissue healing. The polypeptide can be released from the foam to affect contacted tissue. In some aspects, a polypeptide is released from a degradable foam. A polypeptide refers to an oligomer or polymer including two or more amino acid residues, and is intended to encompass compounds referred to in the art as proteins, polypeptides, oligopeptides, peptides, and the like. By way of example, peptides can include antibodies (both monoclonal and polyclonal), antibody derivatives (including diabodies, F(ab) fragments, humanized antibodies, etc.), cytokines, growth factors, receptor ligands, enzymes, and the like. Polypeptides can also include those that are modified with, or conjugated to, another biomolecule or biocompatible compound. For example, the polypeptide can be a peptide-nucleic acid (PNA) conjugate, polysaccharide-peptide conjugates (e.g., glycosylated polypeptides; glycoproteins), a poly(ethyleneglycol)-polypeptide conjugate (PEG-ylated polypeptides).

One class of polypeptides that can be included in the foam is antibodies and antibody fragments. A variety of antibody and antibody fragments are commercially available, obtainable by deposit or deposited samples, or can be prepared by techniques known in the art. For example, monoclonal antibodies (mAbs) can be obtained by any technique that provides for the production of antibody molecules by continuous cell lines in culture. These include, for example, the hybridoma technique (Kohler and Milstein, Nature, 256:495-497 (1975)); the human B-cell hybridoma technique (Kosbor et al., Immunology Today, 4:72 (1983); and the EBV-hybridoma technique (Cole et al., Monoclonal Antibodies and Cancer Therapy, Alan R. Liss, Inc., pp. 77-96 (1985)). Such antibodies may be of any immunoglobulin class including IgG, IgM, IgE, IgA, IgD and any subclass thereof.

Fab or Fab'2 fragments can be generated from monoclonal antibodies by standard techniques involving papain or pepsin digestion, respectively. Kits for the generation of Fab or Fab'2 fragments are commercially available from, for example, Pierce Chemical (Rockford, Ill.).

The polypeptide can also be selected from cell response modifiers. Based on the type of tissue the foam is placed in contact with, an appropriate type of polypeptide that affects a cell response can be chosen.

Cell response modifiers include chemotactic factors such as platelet-derived growth factor (PDGF), pigmented epithelium-derived factor (PEDF), neutrophil-activating protein, monocyte chemoattractant protein, macrophage-inflammatory protein, SIS (small inducible secreted) proteins, platelet factor, platelet basic protein, melanoma growth stimulating activity, epidermal growth factor, transforming growth factor (alpha), fibroblast growth factor, platelet-derived endothelial cell growth factor, insulin-like growth factor, nerve growth factor, vascular endothelial growth factor, bone morphogenic proteins (e.g., BMPs2-7), and bone growth/cartilage-inducing factor (alpha and beta). Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, and activin.

The polypeptide can also be selected from therapeutic enzymes, such as proteases, phospholipases, lipases, glycosidases, cholesterol esterases, and nucleases.

Specific examples include recombinant human tissue plasminogen activator (alteplase), RNaseA, RNaseU, chondroitinase, pegaspargase, arginine deaminase, vibriolysin, sarcosidase, N-acetylgalactosamine-4-sulfatase, glucocerebrocidase, α-galactosidase, and laronidase.

If polypeptides are included in the foam the polypeptides can be present in the form of microparticles (which can be in the polymeric matrix forming the foam structure). Polypeptide microparticles can be formed as described in commonly owned U.S. Patent Application Ser. No. 60/937,492, entitled "Polypeptide Microparticles," and filed on Jun. 28, 2007. Generally, these microparticles are formed in a solution, by coalescing polypeptides with a nucleating agent to form polypeptide nuclei; mixing a phase separation agent with the solution to further coalesce polypeptide around the polypeptide nuclei, thereby forming a mixture; cooling the mixture to form polypeptide microparticles; and removing all or part of the phase separation agent from the polypeptide microparticles. This method has been found to be particularly advantageous for the preparation of microparticles formed predominantly of antibody or antibody fragments, and provides microparticle sets having microparticles of desired sizes, with low size polydispersity, and which maintains good polypeptide activity.

In view of the reactive nature of the members of the redox pair, and members of the gas producing components, these components are typically held as separate compositions (e.g., in separate containers), not in contact with one another until the time that formation of the foam is desired. When the formation of the foam is desired the separate compositions are mixed to form an application composition. In the application composition the members of the redox pair and members of the gas-producing component are mixed with one another in the presence of the macromer material (or materials) to initiate foam formation.

Therefore, as a general matter, the systems of the invention generally include two compositions (e.g., a first composition and a second composition), with the reactive members of the redox pair, and members of the gas producing components separated in these two compositions.

In some modes of practice, a system for the in-situ formation of a biocompatible foam at a tissue site, or a pre-formed foam away from a tissue site, includes a first solution comprising a polymerization activating agent, and an acid; and a second solution comprising a polymerization initiator, and a gas-releasing compound that releases gas upon contact with the acid, being present in a foam-forming amount. In the first or second compositions, or both first and second compositions, a biocompatible macromer is present. The first and second compositions can be combined to form an application composition that is then applied to the tissue in-situ forming a polymer foam for the treatment of the tissue site, or disposed in a mold to form a pre-formed foam.

As a specific example for the formation of a biodegradable foam, the first solution includes ferrous lactate, citric acid, and an α(1→4)glucopyranose-based macromer and the second solution includes hydrogen peroxide, potassium bicarbonate, and a second macromer, such as PEG-based macromer.

As an example of a specific mode of practice, the first composition includes ferrous lactate at a concentration in the range of about 4 mM to about 30 mM, citric acid at a concentration in the range of about 60 mg/mL to about 120 mg/mL, and a and a α(1→4)glucopyranose-based macromer at a concentration in the range of about 500 mg/mL to about 700 mg/mL. The second composition includes hydrogen peroxide at a concentration in the range of about 4 mM to about 30 mM, potassium bicarbonate at a concentration in the range of 60 mg/mL to about 120 mg/mL, and a second macromer, such as PEG macromer, at a concentration in the range of about 350 mg/mL to about 550 mg/mL.

In many aspects the solids components of the compositions will be dissolved or suspended in an aqueous solution. The aqueous compositions may be pH adjusted to provide liquid compositions within desired pH ranges (such as about 6.5 to about 7.5). Other biocompatible liquids, such as dimethyl sulfoxide (DMSO), or biocompatible alcohols, or polyols, can be included in the foam forming compositions.

Pre-formed biocompatible foams of the invention can also be used to treat tissue. "Pre-formed" refers to foams that are not formed in situ, but rather away from a tissue site. A pre-formed biocompatible foam can have a defined structure. For example, a pre-formed biocompatible foam can be created using a mold or casting to provide the foam with a particular shape. Alternatively, a pre-formed biocompatible foam can be created and then shaped as desired, by a process such as cutting. Exemplary shapes useful for tissue treatment include, but are not limited to, spherical, cylindrical, clamshell, flattened, rectangular, square, and rounded shapes.

A pre-formed biocompatible foam can be formed in a manner similar to that used to form a foam in situ, with the exception that the composition is placed in a mixed form, or is mixed, in a receptacle (such as a mold). In the receptacle, the composition generates gas while the macromers polymerize, resulting in a foam that is shaped according to the mold that it is disposed in. After the foam is formed it can be removed from the mold.

Methods of the invention can include the combining, mixing, and disposing of the mixed composition at a target location wherein foam formation is desired. For many compositions of the invention that rapidly form foams, the steps of combining, mixing, and disposing can be performed within a few seconds. Generally, it is desired to perform these steps so that the foam forms as a cohesive mass, rather than a plurality of disparate foam fragments.

In some modes of practice, active mixing is performed to quickly force the blending of the two compositions to form an application composition. Active mixing is typically performed in processes wherein the types and concentrations of components in the application composition result in rapid polymerization of the polymeric materials and gas generation (for example, within a few seconds). Active mixing can be performed using a device having a mechanical feature that rapidly allows a homogenous or substantially homogenous application composition to be formed. As examples, the mechanical feature can be one or more baffles that the compositions are pushed through, a stir bar, and the like.

One type of suitable mixing device comprises injection ports and a chamber having a series of baffles in which the compositions are mixed (Micromedics FibriJet® applicator assemblies and blending tips; commercially available from Micromedics, Saint Paul, Minn.). Mixing of the composition occurs immediately prior to introduction of the mixed compositions into the blending head and does not clog the apparatus.

Alternatively, the compositions can be mixed using passive mixing. Passive mixing refers to those processes wherein a mechanical feature is not used to force the compositions together. Instead, in passive mixing, compositions are allowed to mix with each other. For example, mixing of the components can occur more by diffusion in passive mixing than in active mixing.

After the compositions have been mixed by an active mixing process or by a passive mixing process, the application composition can be applied in situ to a tissue site or can be placed in a receptacle to form a foam.

The application composition can be rapidly applied to a tissue site, such as a wound, where it quickly forms a biocompatible foam. In some modes of practice the composition is delivered to the tissue site at a rate of about 2 mL/sec. The rate of delivery of the application composition can be increased by utilizing a larger conduit or multiple conduits.

Optionally, the biocompatible foams of the invention can be used in conjunction with an implantable medical article made of a material that is different than the foam. A biocompatible foam of the invention can be prepared by a method so a portion of the foam material is associated with a surface of the implantable medical article. In some modes of practice, the mixed foam-forming composition is applied to a surface of an implantable medical article, and while the foam is generated it becomes associated with the surface.

In some cases, the implantable medical article can provide a structural support for the foam. In other words, the article can provide a scaffolding or framework on which the foam is placed. This can be desirable in applications wherein it is desired to use a biocompatible foam, but the foam itself cannot provide a desired degree of structural properties needed for medical treatment.

Examples of implantable medical article which the foam can be associated with include but are not limited to vascular implants and grafts, grafts, surgical devices, synthetic prostheses, vascular prosthesis including endoprosthesis, stent-graft, and endovascular-stent combinations, small diameter grafts, abdominal aortic aneurysm grafts, wound dressings and wound management device, hemostatic barriers, mesh and hernia plugs, patches, including uterine bleeding patches, atrial septal defect (ASD) patches, patent foramen ovale (PFO) patches, ventricular septal defect (VSD) patches, and other generic cardiac patches, ASD, PFO, and VSD closures, percutaneous closure devices, mitral valve repair devices, left atrial appendage filters, valve annuloplasty devices, catheters, central venous access catheters, vascular access catheters, parenteral feeding catheters, stroke therapy catheters, anastomosis devices and anastomotic closures, aneurysm exclusion devices, birth control devices, breast implants, cardiac sensors, infection control devices, membranes, tissue scaffolds, tissue-related materials, shunts including cerebral spinal fluid (CSF) shunts, glaucoma drain shunts, ear devices such as ear drainage tubes, ophthalmic devices, cuffs and cuff portions of devices including drainage tube cuffs, implanted drug infusion tube cuffs, catheter cuff, sewing cuff, spinal and neurological devices, nerve regeneration conduits, neurological catheters, neuropatches, orthopedic devices such as orthopedic joint implants, bone repair/augmentation devices, cartilage repair devices, urological devices and urethral devices such as urological implants, bladder devices, renal devices and hemodialysis devices, biliary drainage products, abscess drainage catheters, drug infusion catheters, dental devices and dental implants, tympanostomy vent tubes, abscess drainage catheters, drug infusion catheters, dental devices and dental implants, and tympanostomy vent tubes.

The article that the foam can be associated with can be fabricated from textiles, which include woven materials, knitted materials, and braided materials. Examples of implantable article made from fabrics include cardiac patches, sheaths, and grafts.

The article that the foam can be associated with can also have a porous surface, such as the porous surface of a graft, sheath, cover, patch, sleeve, wrap, or casing.

Testing can be carried out to determine mechanical properties of the biocompatible foam. Dynamic mechanical thermal testing can provide information on the viscoelastic and Theological properties of the biocompatible foam by measuring its mechanical response as it is deformed under stress. Measurements can include determinations of compressive modulus, and shear modulus. Key viscoeslatic parameters (including compressive modulus and sheer modulus) can be measured in oscillation as a function of stress, strain, frequency, temperature, or time. Commercially available rheometers (for example, available from (TA Instruments, New Castle, Del.) can be used to make these measurements. The testing of hydrogels for mechanical properties is also described in Anseth et al. (1996) *Mechanical properties of hydrogels and their experimental determination*, Biomaterials, 17:1647.

The biocompatible foam can be measured to determine its complex dynamic modulus ($G^*$): $G^* = G' + 1G'' = \sigma^*/\gamma^*$, where $G'$ is the real (elastic or storage) modulus, and $G''$ is the imaginary (viscous or loss) modulus, these definitions are applicable to testing in the shear mode, where G refers to the shear modulus, $\sigma$ to the shear stress, and $\gamma$ to the shear strain.

In some aspects the biocompatible biostable foams have a compressive modulus in the range of about 5 kPa to about 200 kPa, and more specifically in the range of about 30 kPa to about 150 kPa.

In some aspects the biodegradable biocompatible foams have a compressive modulus in the range of about 0.5 kPa to about 50 kPa, and more specifically in the range of about 3 kPa to about 30 kPa.

In some aspects the biocompatible biostable foams have 50% compressive force in the range of about 1 N to about 50 N, and more specifically in the range of about 5 N to about 30 N.

In some aspects the biodegradable biocompatible foams have 50% compressive force in the range of about 0.5 N to about 20 N, and more specifically in the range of about 1 N to about 6 N.

The porous structure of the inventive foams can be described in terms of pore volume, which is the ratio of the foam's air volume to the foam's total volume. Pore volume can also be calculated knowing the density of the polymerized materials in foam form versus the density of the polymerized materials in solid (non-foamed) form.

For example, to determine the pore volume of a particular foam, polymerization of the macromer materials can be carried out in the presence of the gas-producing components (which lead to a foam product), and in the absence of the gas-producing components (which lead to a solid, non-foamed product; i.e., one without pores). The polymeric components are identical in the foamed and solid product. After polymerization of the foamed and non-foamed solid takes place, the dimensions of the foamed and solid products are measured, and each are weighed. The density is calculated by the weight divided by the volume of the product. Pore volume is then calculated by the ratio of the density of the solid, non-foamed, product to the density of the foamed product. For example, if the density of the solid product is 1.0 g/cm$^3$, and the density of the foamed product is 0.25 g/cm$^3$, the pore volume for the foamed product is 4. A larger pore volume number generally means the foamed product relatively has a greater number of air pockets, larger air pockets, or both.

The macromer materials described herein can be used to create a biocompatible foam having a pore volume within a broad range. For example, in some aspects a biocompatible foam of the invention can have a pore volume in the range of about 7.5 to about 1.5, in the range of about 7.0 to about 1.75, in the range of about 6.5 to about 2.0, or in the range of about 6.0 to about 2.25.

In some aspects the biocompatible foam is biodegradable and has a pore volume in the range of about 7.5 to about 1.5, in the range of about 7.0 to about 1.75, in the range of about 6.5 to about 2.0, or in the range of about 6.0 to about 2.25.

In some aspects the biocompatible foam is biostable and has a pore volume in the range of about 7.5 to about 1.5, in the range of about 7.0 to about 1.75, in the range of about 6.5 to about 2.0, or in the range of about 6.0 to about 2.25.

Once formed, the biocompatible foam can serve as a cell scaffolding. In many instances, the foam is formed or placed at a target site where it is associated with tissue. After a period of time the pores of the foam can become infiltrated with cells from the body. Alternatively, or additionally, the foam can be provided with exogenous cells and formed or placed at a tissue site.

The biocompatible foam, serving as a cell scaffolding, can promote the tissue repair, can augment tissue, or can replace the tissue at the target site. In many cases, foam will be formed or will be placed near, on, or in a tissue targeted so that the normal wound healing response is enhanced. Without the foam healing process may otherwise result in nonfunctional scar tissue. In the case of a biodegradable foam, following a period of time in contact with the target tissue, the foam typically undergoes degradation. Before, during, or after degradation, tissue repair can be promoted.

For example, the foam can promote remodeling of surrounding tissues within a mammalian host. Thus, in some aspects, the cell scaffolding can function to promote tissue replacement, and also function as a remodeling template for tissue repair.

The biocompatible foams of the invention can have properties suitable for repair and/or replacement of host tissues when implanted, including chemical, physical and/or structural properties. Illustrative chemical properties of the biocompatible foams include chemistries that are suitable for cell attachment and growth when the foam is implanted or formed within a subject. Illustrative physical properties include mechanical properties similar to those of the tissue at the site of implantation or formation.

The biocompatible foams can include components such as cell attachment factors, growth factors, and/or cytokines. These components can be useful for maintaining the viability of the cells, and/or for promoting a cellular response that is a part of the tissue regeneration process.

The biocompatible foams can be used in a variety of applications to treat various types of disruptions to tissue, including tissue injuries, intentionally or accidentally induced, including wounds.

The biocompatible foams can be used to treat abrasions, lacerations, open wounds, and deep wounds. The biocompatible foams can be used to treat tissue disruptions that have infection, or that are not infected.

The foams of the invention can be used for the treatment of the following tissue disruptions: burns, including common burns, first degree, second degree, and third degree burns; abrasions; tissue injuries caused from chemical or electrical contact; decubitus (bed sores), frostbite, gangrene, weapon (e.g., gunshot or knife) wounds, ulcers osteomyelitis (infection of bone or bone marrow); psoriatic lesions; acne, carbuncles, erysipelas (dermal streptococcus infection), abscesses, blisters; pilonidal cysts; acute hand infections such as paronychia and felon.

The foams of the invention can also be used in plastic or cosmetic surgical procedures. For example, the biocompatible forms can be used to augment breast tissue, or tissues in the lip, chin, or cheek areas.

The foams can be formed in situ following a surgical procedures such as a thoracotomy (chest incision), a fasciotomy (removal or cutting of the fascia to relieve tension or pressure), a tracheotomy (incision in the neck to access the trachea), a laparotomy or coeliotomy (surgical incision through the abdominal wall), an escharotomy (an incision through the eschar to treat severe burns), an episiotomy (an incision through the perineum, often performed to facilitate childbirth), a hysterotomy (uterine incision), a myotomy (muscle incision), or an osteotomy (cutting of the bone).

Alternatively, a pre-formed foam can be applied to the tissue site following any one of the above procedures or incidents.

As one example, the biocompatible foam is used in a method for treating a cutaneous wound. The cutaneous wound could be any wound to the dermal layers of the skin that is accidentally or intentionally incurred. Of particular benefit of the methods and compositions of the invention is the in situ treatment of wounds of considerable depth and/or area. This is because the foams can be formed in situ to have significant depth and area. At the same time, the foams of the invention, while occupying a larger volume, can also maintain a strong structure with a generally uniform porous structure throughout.

For example, the wound to be treated with the foam of the invention can have a depth of about 0.5 cm or greater, about 1.0 cm or greater, about 1.5 cm or greater, or about 2.5 cm or greater, such as in the range of about 0.5 cm to about 2.5 cm. The wounds can also be multiple centimeters in width and length. The amount of composition in the liquid form that is applied to the wound site can depend on the size of the wound. Given the advantageous properties of the foamed form, it is reasonable to apply to the wound site multiple milliliters or multiple centiliters of foam-forming liquid composition to the wound site.

Accordingly, in some modes of practice, a foam formed at the cutaneous wound site can have a thickness of about 0.5 cm to about 2.5 cm.

Various factors can influence the decision of how long to treat the tissue with the foam of the invention. These include (for biodegradable foams) the rate of degradation of the foam in contact with tissue, the size of the tissue site (e.g., wound) to be treated, the type of tissue treated (e.g., dermal tissue versus osseous tissue), the type of tissue disruption or injury, the optional use of other medical articles in combination with the foam. Tissue healing can be monitored during the course of foam application. The foam can be removed, or a new foam can be formed at the tissue site at a desired time period. For example, a degradable foam could be replaced after a period of time depending on the rate of degradation. If the foam degrades and the tissue is not yet healed a subsequent foam can be formed on the tissue site to continue to promote tissue healing. The foam can be left in contact with the tissue for a period of days, weeks, or months depending on one or more of the above factors.

In some aspects, the treatment of a cutaneous wound site can first involve a debridement process. Debridement of the wound site can be carried out before a biocompatible foam of the invention is formed on the site and left for a period of time to promote wound healing. The purpose of the debridement process can be to remove necrotic tissue and generally clean the wound. In the process, dead spaces in the wound are reduced, which prevents further bacterial growth. Debridement thereby reduces wound contamination and continued tissue destruction. Debridement can allow healthy granulation tissue to form.

Debridement procedures can be divided into two major groupings: physical debridement and chemical debridement. Examples of physical debridement include wet-to-dry dressings, pressurized irrigation, and surgical or sharp techniques. Chemical debridement can be performed using enzymes such as collagenase and trypsin to remove eschar from wounds.

In some aspects of the invention a method for treating a wound site is performed using a combination debridement and wound healing processes. Both processes make use of foam-forming compositions. Macromer materials, including the alkoxyalkane polymer-based macromers such as poly (ethylene glycol) (PEG) macromers described herein as useful for wound healing can also be used in the debridement process. In some modes of practice, the debridement process forms a biostable foam, which is then removed along with the unwanted debris from the wound. Next, a biodegradable foam is created on the debrided tissue site and left there for a period of time to promote wound healing.

In the debridement process, macromer, polymerization initiator, and gas producing components of the system are mixed and then applied in situ as an application composition to a wound site on a subject. The gas production provides at least physical action, loosening matter on the wound site (such as necrotic tissue or other foreign matter that may be present) so that it can be driven up into the mass of polymerized foam that is being formed. After a period of time, a solid polymer foam is formed on the wound site that contains the lifted wound materials. The polymer foam can easily be removed from the wound site, and can carry away the loosened matter that is suspended in the foam. The process can be carried out without injuring the underlying tissue. The macromer component of the debridement process can also be chosen to provide a desired degree of exudate absorption at the wound site. The debridement process can further include a proteolytic enzyme useful for breaking up the necrotic tissue, which typically causes the wound to produce excess exudate.

After the wound is debrided, another foam composition can be formed on the tissue to promote healing according to the compositions and methods described herein.

In some processes, after the foam has been applied to the wound site a body fluid and cells associated with the epidermis and dermis of the skin at the wound site can begin to infiltrate the pores. Cells involved in the healing process, such as red blood cells, platelets, and polymorphonuclear cells (PMNs) can become associated with the biocompatible foam structure. Fluid components such as plasma proteins and vasoactive amines can also infiltrate the pores of the foam. Fibrinolytic events can cause the deposition of fibrin throughout the porous matrix of the foam. Growth factors, such as platelet-derived growth factor (PDGF) and transforming growth factor $\beta$ (TGF-$\beta$) can also be produced by platelets and deposited in the pores of the foam. The PMNs are attracted to the site by the growth factors and promote a healing inflammatory process. Further, macrophages are attracted to the foam and with the PMNs being to form an extracellular matrix. Subsequently, fibroblasts that are recruited to the pores of the foam by the growth factors produce collagen further advancing the tissue healing process in the foam.

In some cases the wound is filled with a composition that forms a biodegradable foam. The biodegradable promotes tissue healing by, in the least, providing a scaffolding for the body's cells that are involved in the healing process. The course of events involving the cells and factors involved in the healing process can occur as described above. Also, over time, degradation of the biodegradable foam, as caused by the enzymatic degradation of the α(1→4)glucopyranose segments of the crosslinked polymeric matrix, causes the thinning of the walls of the foam. During the healing process, the materials of the foam are slowly removed by this degradation process and are replaced by the components of the healing process (cells and tissue material that is produced by the cells). Eventually, continued degradation results in loss of the porous structure, but the body's natural tissue repair components have infiltrated the foam and advance healing to a point where the foam structure is no longer needed. The materials that were used to form the biodegradable foam can be consumed by the cellular material at the treated wound site and/or removed from the wound site (and eventually the body) after a period of time.

In other cases the wound is filled with a composition that forms a biostable foam. The biostable foam can also promotes tissue healing by, in the least, providing a scaffold for the body's cells that are involved in the healing process. During the course of events involving the cells and factors involved in the healing process can occur as described above. However, over time, the materials of the biostable foam remain in place. Eventually, the body's natural tissue repair components infiltrate and integrate into the foam. In some aspects the healed wound site includes the foam.

As another example, the biocompatible foam is used in a method for treating osseous tissue. Osseous tissue (also referred to herein as bone tissue or bone) is mainly formed of mineralized connective tissue. Osseous tissue typically includes a collagen fiber matrix and deposited calcium salts in the form of hydroxyapatite. Osseous tissue includes compact bone tissue (found normally on the hard exterior of bones) and spongy bone tissue (found normally on the interior of bones).

A biocompatible foam according to the invention can be placed in contact with osseous tissue to promote bone healing. The biocompatible foam can be formed in situ at a target site on a bone during an orthopedic surgical procedure. The biocompatible foam can be formed in an open cavity procedure. Alternatively, a pre-formed form and be placed at a target site on a bone. Biocompatible or biodegradable foams can be used to treat osseous tissue and promote repair. Exemplary orthopedic sites for form formation or application include the knee, hip, hands, feet, shoulder, and spine.

In some modes of practice, the biocompatible foam is used as a bone filler. For example, a surgical process may require the removal of a portion of a bone resulting in a void, cavity, or hole in the bone. An in situ foam forming composition can be delivered to the hole in the bone to create a foam which fills the hole. In other modes of practice, the biocompatible foam is used as a bone cement to facilitate the joining of bone fragments.

The biocompatible foam can be prepared to include particulates that become associated or entrapped in the polymeric matrix of the foam, and that facilitate healing of the osseous tissue. It is known in the art to use bone particulates and bone minerals with synthetic material to promote healing of bone tissue. For example, WO00/045871 describes collagen sponge with bone particulates formed by freeze-drying a slurry of collagen with cortical bone chips. U.S. Pat. No. 4,863,472 describes the preparation of bone graft implants made of polyglycolide-type polymers including hydroxyapatite powder.

The particulates can include one or more components, such as minerals, that are typically deposited during formation of new osseous tissue. For example, the particulates can be natural bone chips or granules, or calcium phosphate chips. Exemplary particulates have an average particle size in the range of about 0.5 mm to about 2 mm. Biocompatible foams for the treatment of osseous tissue are desirably flexible and strong. In exemplary embodiments the foams comprise a poly(alkylene oxide), such as PEG.

A biocompatible foam with particulates, such as one having calcium phosphate chips and useful for healing bone tissue, can be formed in situ by resuspending the particulates while the foam is forming. For example, particulates can be placed in a cavity in the bone and then the mixed, foam-forming composition can be forcefully injected into the cavity, causing resuspension of the particulates. Because the composition can rapidly form a foam (e.g., in a matter of seconds), the particulates do not settle out of the composition and become entrapped in the foam mass. Other methods for forming a particulate containing in situ-formed foam can be performed using a triple barrel syringe, in which one of the barrels includes the particulates. Other methods for forming a particulate containing in situ-formed foam can be performed using a foam forming composition having an increased viscosity.

If the biocompatible foams are formed or implanted at a location on or within the heart (an organ that is constantly in motion), the biocompatible foams can be selected to possess mechanical properties that will allow it to move with the patient heart tissue while providing the structural integrity for the desired treatment. The foam can also confer additional mechanical properties to increase the mechanical strength of the damaged tissue, thus reducing wall stress.

The biocompatible foams of the present invention can also be used in combination one or more other medical articles that promote tissue healing. For example, the biocompatible foams can be used in combination with bandages, tapes, and other wound dressings, which can be adhesive or non-adhesive.

The biocompatible foams of the present invention can also be used in combination one or more other medical articles that assist in wound closure. For example, the biocompatible foams can be used in combination with staples, sutures, Steri-Strips™ (3M Health Care, St. Paul, Minn.), and negative pressure wound therapy devices. Biostable and biodegradable sutures are well known in the art and are commercially available from, for example, Ethicon, Inc. (Somerville, N.J.). Negative pressure and suction wound therapy devices are also well known in the art and have been described in, for example, U.S. Pat. No. 4,969,880 (Zamierowski), and U.S. Pat. No. 5,636,643 and U.S. Pat. No. 5,645,081 (Argenta et al.). The foams of the present invention can be placed beneath components of the negative pressure device and in contact with the tissue being treated.

The invention will be further described with reference to the following non-limiting Examples.

Example 1

Maltodextrin-Methacrylate/Poly(Ethylene Glycol) Diacrylate Degradable Foam

The REDOX solutions used to initiate polymerization were prepared directly before use. An 8 mM solution of hydrogen peroxide (Sigma-Aldrich, St. Louis, Mo.) was prepared in deionized water. In addition, an 8 mM solution of ferrous lactate (Sigma-Aldrich, St. Louis, Mo.) was prepared in deionized water. Both solutions were subjected to vortexing prior to use. Maltodextrin-methacrylate (MD-MA) with a degree of substitution of ~0.14 (0.14 mmol/gram, methacrylate/maltodextrin) was dissolved in the ferrous lactate solution at a concentration of 600 mg/mL. Poly(ethylene glycol)$_{700}$ diacrylate (PEGDA) (Sigma-Aldrich, St. Louis, Mo.) was dissolved into the hydrogen peroxide reagent at a concentration of 450 mg/mL.

Into the hydrogen peroxide solution, potassium bicarbonate (Sigma-Aldrich, St. Louis, Mo.) was dissolved at a concentration of 100 mg/mL. Additionally, 100 mg/mL of citric acid (Sigma-Aldrich, St. Louis, Mo.) was added to the ferrous lactate solution. It is important to note that the bicarbonate must be added to the peroxide reagent because both compounds are slightly basic and there will be no adverse reaction. The solutions were vortexed completely before polymerization. The total concentrations of the macromer materials in the mixed composition (prior to being polymerized by reaction) was maltodextrin-methacrylate: 300 mg/mL; poly(ethylene glycol)$_{700}$-diacrylate: 225 mg/mL.

Approximately 1.5 mL of each the PEGDA and MDMA components were loaded into separate 3 mL disposable syringes. The syringes were then attached to a Micromedics FibriJet blending connector and placed into a plastic Micromedics housing kit. A 21 gauge needle was placed on the tip of the blending connector. Immediately as the solutions were equally ejected from the syringe needle, vigorous gas formation occurred simultaneously as polymerization occurred. The foam was completely set up in less than 3 seconds. The final product was pale yellow in color and had a very fine porous structure.

Examples 2-9

Maltodextrin-Methacrylate/Poly(Ethylene Glycol) Diacrylate Degradable Foams with Variable Porosity and Properties Biodegradable foams were prepared as described in Example 1 with the changes in the concentrations of maltodextrin-methacrylate, poly(ethylene glycol)$_{700}$-diacrylate, citric acid, and potassium bicarbonate, as reflected in Table 1. Also, potassium persulfate replaced hydrogen peroxide as the initiator, and the redox components were used at a concentration of 6 mg/mL. The concentrations of the macromer materials (prior to being polymerized by reaction) listed in Table 1 are in the application (mixed) compositions and therefore represent the final concentrations; concentrations in the pre-mixed composition are double those shown in the Table 1.

A TA.XT™ Plus Texture Analyzer (Stable Micro Systems; distributed by Texture Technologies Corp; Scarsdale, N.Y.), which is an instrument used in compressive and tensile testing applications, was used to perform rheological testing. The physical properties of the foams (stress and compression force testing) were carried out using the texture analyzer with a 2.5" diameter aluminum cylindrical probe. The trigger force was 4 grams and the test speed was 1 mm/sec. Once the trigger force was reached, it measured 50% of the foam height as compared to the calibration depth. The stress is the force/area of the foam (2 cm×2 cm).

TABLE 1

| Example | Maltodextrin Methacrylate (mg/mL) | PEG-DA 700 (mg/mL) | Citric Acid (mg/mL) | Potassium Bicarbonate (mg/mL) | Stress (Kpa) | Force (N) |
|---|---|---|---|---|---|---|
| 2 | 250 | 200 | 35 | 35 | 4.2 | 1.7 |
| 3 | 250 | 250 | 35 | 35 | 4.8 | 1.9 |
| 4 | 250 | 200 | 40 | 40 | 2.8 | 1.1 |
| 5 | 250 | 250 | 40 | 40 | 5.9 | 2.4 |
| 6 | 250 | 200 | 45 | 45 | 2.2 | 0.9 |
| 7 | 250 | 250 | 45 | 45 | 3.1 | 1.3 |
| 8 | 250 | 200 | 50 | 50 | 2.7 | 1.1 |
| 9 | 250 | 250 | 50 | 50 | 3.1 | 1.2 |

Examples 10-23

Maltodextrin-Methacrylate/Poly(alkylene oxide) Degradable Foams

Biodegradable foams were prepared as described in Example 1 with the changes in the concentrations of maltodextrin-methacrylate, the type and concentration of the poly(alkylene oxide) as reflected in Table 2. In these examples, all foams were made using 80 mg/mL citric acid and potassium bicarbonate as foaming agents, and 6 mg/mL potassium persulfate and ferrous gluconate as initiators.

The physical properties of the foams (stress and compression force testing) were carried out using a TAXT2 texture analyzer with a 2.5" diameter aluminum cylindrical probe. The trigger force was 4 grams and the test speed was 1 mm/sec. Once the trigger force was reached, it measures 50% of the foam height as compared to the calibration depth. The stress is the force/area of the foam (2 cm×2 cm).

The concentrations of the macromer materials (prior to being polymerized by reaction) listed in Table 2 are in the application (mixed) compositions and therefore represent the final concentrations; concentrations in the pre-mixed composition are double those shown in the Table 2.

TABLE 2

| Example | Maltodextrin Methacrylate (mg/mL) | Poly(alkylene oxide) Macromer | | Stress (KPa) | Force (N) |
| | | Type | (mg/mL) | | |
|---|---|---|---|---|---|
| 10 | 250 | Branched | 250 | 3.337 | 1.334 |
| 11 | 300 | PEG triacrylate | 250 | 3.286 | 1.314 |
| 12 | 200 | | 150 | 2.505 | 1.002 |
| 13 | 250 | PEG-DA 700 | 300 | 3.446 | 1.378 |
| 14 | 300 | | 300 | 5.598 | 2.239 |
| 15 | 200 | | 150 | 1.231 | 0.492 |
| 16 | 250 | PEG-DA 575 | 300 | 20.469 | 8.185 |
| 17 | 300 | | 300 | 9.868 | 3.947 |
| 18 | 200 | | 150 | 3.942 | 1.577 |
| 19 | 250 | PEG-DMA 550 | 300 | 36.078 | 14.427 |
| 20 | 300 | | 300 | 14.500 | 5.799 |
| 21 | 200 | | 150 | 30.746 | 12.298 |
| 22 | 250 | PEG-DA 250 | 300 | 3.325 | 1.330 |
| 23 | 200 | | 150 | 1.347 | 0.539 |

Examples 24-44

Biocompatible Foam Initiator Systems

Biostable foams were prepared as described in Example 1. The compositions for forming the biostable foams used a branched PEG triacrylate (as opposed to maltodextrin-methacrylate, which was used with the biodegradable foams). The types and concentrations of the macromer materials in the mixed composition were as follows: branched PEG triacrylate: 300 mg/mL; poly(ethylene glycol)$_{700}$-diacrylate: 225 mg/mL; The concentrations of redox materials listed in Table 3 represent their concentrations in the pre-compositions (i.e., the first and second compositions). Changes in the type and concentration of polymerization initiator and activator used are noted in Table 3; potassium persulfate was used as the initiator.

The physical properties of the foams (stress and compression force testing) were carried out using a TAXT2 texture analyzer with a 2.5" diameter aluminum cylindrical probe. The trigger force was 4 grams and the test speed was 1 mm/sec. Once the trigger force was reached, it measured 50% of the foam height as compared to the calibration depth. The stress is the force/area of the foam (2 cm×2 cm).

TABLE 3

| Example | [O] | mmol [O] | mmol [R]$^a$ | Setup Time |
|---|---|---|---|---|
| 24 | Fe$^{2+}$ Gluconate | 2.241 | 2.242 | 2-3 sec |
| 25 | | 6.724 | 6.722 | 1 sec |
| 26 | | 11.207 | 11.205 | 1 sec |
| 27 | Fe$^{2+}$ Ascorbate | 2.463 | 2.460 | 10 sec |
| 28 | | 4.925 | 4.924 | 5-6 sec |
| 29 | | 14.775 | 14.775 | 1-2 sec |
| 30 | Fe$^{2+}$ Acetylacetonate | 3.936 | 3.936 | $b$ |
| 31 | | 7.872 | 7.872 | 4 sec$^c$ |
| 32 | | 11.808 | 11.808 | 3 sec$^c$ |
| 33 | Fe$^{2+}$ Fumarate | 5.886 | 5.886 | $d$ |
| 34 | | 8.829 | 8.829 | $d$ |
| 35 | | 11.772 | 11.772 | $d$ |
| 36 | Mg$^{2+}$ D-Gluconate | 2.412 | 2.412 | $e$ |
| 37 | | 7.236 | 7.236 | $e$ |
| 38 | | 12.060 | 12.060 | $e$ |
| 39 | Cu$^{2+}$ D-Gluconate | 2.203 | 2.203 | $e$ |
| 40 | | 6.610 | 6.610 | $e$ |
| 41 | | 11.017 | 11.017 | $e$ |
| 42 | Fe$^{2+}$ Lactate | 4.274 | 4.274 | 4 sec$^f$ |
| 43 | | 8.547 | 8.547 | ~3 sec$^g$ |
| 44 | | 12.821 | 12.821 | 1 sec$^h$ |

$^a$potassium persulfate
$^b$5 sec to gel, no foam structure
$^c$Foam: some pores but flat
$^d$Fe$^{2+}$ Fumarate did not dissolve
$^e$Did not polymerize
$^f$Foam: porous but not thick
$^g$Foam: thicker than Ex 42
$^h$Foam: 15 mm thick, porous

Example 45

Maltodextrin-Methacrylate/Poly(ethylene glycol) Monomethyl Ether Monomethacrylate/Surfactant Degradable Foam The REDOX solutions used to initiate polymerization were prepared directly before use. A 12 mM solution of hydrogen peroxide (Sigma-Aldrich, St. Louis, Mo.) was prepared in deionized water. In addition, a 12 mM solution of ferrous lactate (Sigma-Aldrich, St. Louis, Mo.) was prepared in deionized water. Both solutions were subjected to vortexing prior to use. Maltodextrin-methacrylate (MDMA) with a degree of substitution of 0.14 was dissolved in the ferrous lactate solution at a concentration of 600 mg/mL. Poly(ethylene glycol)$_{1000}$ monomethyl ether monomethacrylate (PEG-MEMA) was dissolved into the hydrogen peroxide reagent at a concentration of 450 mg/mL.

Into the hydrogen peroxide solution, potassium bicarbonate (Sigma-Aldrich, St. Louis, Mo.) was dissolved at a concentration of 100 mg/mL. Approximately 7 mg/mL of Pluronic 25R4 (BASF) was added to this solution as well. Additionally, 100 mg/mL of citric acid (Sigma-Aldrich, St. Louis, Mo.) was added to the ferrous lactate solution. The solutions were vortexed completely before polymerization.

The final concentrations of the macromer and surfactant materials in the mixed composition were as follows: branched MDMA: 300 mg/mL; PEG-MEMA: 225 mg/mL; potassium bicarbonate: and Pluronic 25R4: 3.5 mg/mL.

Approximately 1.5 mL of each the PEG-MEMA and MDMA components were loaded into separate 3 mL disposable syringes. The syringes were then attached to a Micromedics FibriJet blending connector and placed into a plastic Micromedics housing kit. A 21 gauge needle was placed on the tip of the blending connector. Immediately as the solutions were equally ejected from the syringe needle, vigorous gas formation occurred simultaneously as polymerization occurred. The foam was completely set up in less than 3 seconds. The final product was pale yellow in color and had a soft and porous structure.

Example 46

Poly(ethylene glycol) Trimethylolpropane Ethoxylate Triacrylate/Poly(ethylene glycol) Diacrylate Biostable Foam The REDOX solutions used to initiate polymerization were prepared directly before use. A 2 mM solution of hydrogen peroxide was prepared in deionized water. In addition, a 2 mM solution of ferrous lactate was prepared in deionized water. Both solutions were subjected to vortexing prior to use. Poly(ethylene glycol) trimethylolpropane ethoxylate triacrylate (PEGTA) was dissolved in the ferrous lactate solution at a concentration of 400 mg/mL. Poly(ethylene glycol)$_{700}$ diacrylate (PEG-DA) was dissolved into the hydrogen peroxide reagent at a concentration of 400 mg/mL.

Into the hydrogen peroxide solution, potassium bicarbonate (Sigma-Aldrich, St. Louis, Mo.) was dissolved at a concentration of 100 mg/mL. Additionally, 100 mg/mL of citric acid (Sigma-Aldrich, St. Louis, Mo.) was added to the ferrous lactate solution. The solutions were vortexed completely before polymerization.

The final concentrations of the macromer materials in the mixed composition were as follows: branched PEGTA: 200 mg/mL; PEG-DA: 200 mg/mL.

Approximately 1.5 mL of each the PEGDA and PEGTA components were loaded into separate 3 mL disposable syringes. The syringes were then attached to a Micromedics FibriJet blending connector and placed into a plastic Micromedics housing kit. A 21 gauge needle was placed on the tip of the blending connector. Immediately as the solutions were equally ejected from the syringe needle, vigorous gas formation occurred simultaneously as polymerization occurred. The foam was completely set up in less than 3 seconds. The final product was light yellow in color and had a very fine porous structure.

Examples 47-64

Poly(ethylene glycol) Trimethylolpropane Ethoxylate Triacrylate/Poly(alkylene oxide) Biostable Foams Biostable foams were prepared in a method as described in Example 46 with the changes in the concentrations of PEGTA, the type and concentration of poly(alkylene oxide) macromer (as shown in Table 4), the amount of citric acid and potassium bicarbonate (80 mg/mL), and the amount of ferrous gluconate and potassium persulfate (6 mg/mL).

The physical properties of the foams (stress and compression force testing) were carried out using a TAXT2 texture analyzer with a 2.5" diameter aluminum cylindrical probe. The trigger force was 4 grams and the test speed was 1 mm/sec. Once the trigger force was reached, it measured 50% of the foam height as compared to the calibration depth. The stress is the force/area of the foam (2 cm×2 cm).

TABLE 4

| Example | $PEG_{1150}TA$ | Poly(alkylene oxide) Macromer type | mg/mL | Stress (KPa) | Force (N) |
|---|---|---|---|---|---|
| 47 | 300 mg/mL | PEG-DA 250 | 250 | 56 | 22.4 |
| 48 | | | 350 | 19.2 | 7.07 |
| 49 | 300 mg/mL | PPG-DA 540 | 250 | 12.5 | 5 |
| 50 | | | 350 | 27.3 | 10.9 |
| 51 | 300 mg/mL | PPG-DMA 475 | 250 | 14.4 | 5.8 |
| 52 | | | 350 | 12 | 4.8 |
| 53 | 300 mg/mL | PPG-DA 900 | 250 | 11.2 | 4.5 |
| 54 | | | 350 | 7.1 | 2.8 |
| 55 | 300 mg/mL | PEG-DMA 750 | 250 | 68.6 | 27.4 |
| 56 | | | 350 | 20.6 | 8.2 |
| 57 | 300 mg/mL | PEG-DA 575 | 250 | 75.7 | 30.3 |
| 58 | | | 350 | 93.2 | 37.3 |
| 59 | 300 mg/mL | PEG-DMA 550 | 250 | 60.3 | 24.1 |
| 60 | | | 350 | 39.2 | 15.7 |
| 61 | 300 mg/mL | PEG-DA 700 | 250 | | |
| 62 | | | 350 | | |
| 63 | 600 mg/mL | PEG-DA 1000 | 250 | | |
| 64 | | | 350 | | |

Example 65

Pore Volumes of Biodegradable Foams

The pore volumes of degradable foams were determined by polymerizing maltodextrin-methacrylate (MD-MA)/poly(ethylene glycol) diacrylate (PEG-DA) or poly(ethylene glycol) monomethyl ether monomethacrylate (PEG-MEMA) compositions in the presence and absence of the gas producing component.

Foam A was prepared according to Example 1. Solid A was prepared according to Example 1 but without the potassium bicarbonate and citric acid.

Foam B was prepared according to Example 45. Solid B was prepared according to Example 45 but without the potassium bicarbonate and citric acid.

Results are shown in Table 5

TABLE 5

| | Weight (g) | L (cm) | W (cm) | H (cm) | Volume ($cm^3$) | Density ($g/cm^3$) |
|---|---|---|---|---|---|---|
| Foam A | | | | | | |
| 1 | 0.1557 | 1 | 0.89 | 0.72 | 0.6 | 0.243 |
| 2 | 0.1996 | 1 | 0.96 | 0.84 | 0.8 | 0.248 |
| 3 | 0.152 | 0.9 | 0.88 | 0.82 | 0.6 | 0.234 |
| | | | | | avg | 0.242 |
| | | | | | stdev | 0.007 |
| Foam B | | | | | | |
| 1 | 0.2712 | 1.567 | 0.91 | 0.91 | 1.3 | 0.209 |
| 2 | 0.2673 | 1.65 | 0.9 | 0.99 | 1.5 | 0.182 |
| 3 | 0.2558 | 1.57 | 0.99 | 0.89 | 1.4 | 0.185 |
| | | | | | avg | 0.192 |
| | | | | | stdev | 0.015 |

| | Weight (g) | Diameter (cm) | Radius (cm) | H (cm) | Volume ($cm^3$) | Density ($g/cm^3$) |
|---|---|---|---|---|---|---|
| Solid A | | | | | | |
| 1 | 0.6739 | 1.2 | 0.6 | 0.641 | 0.7 | 0.930 |
| 2 | 0.6257 | 1.2 | 0.6 | 0.581 | 0.7 | 0.953 |
| | | | | | avg | 0.941 |
| | | | | | stdev | 0.016 |
| Solid B | | | | | | |
| 1 | 1.068 | 1.2 | 0.6 | 0.812 | 0.9 | 1.164 |
| 2 | 0.9947 | 1.2 | 0.6 | 0.846 | 1.0 | 1.040 |
| | | | | | avg | 1.102 |
| | | | | | stdev | 0.087 |

The percent solids in foam A was 25.66% and 17.42% in foam B. Pore volume is calculated at 3.89 for foam A, and 5.74 for foam B.

Example 66

Pore Volume of a Biostable Foam

The pore volumes of a biostable form was determined by polymerizing a poly(ethylene glycol) trimethylolpropane ethoxylate triacrylate (PEG-TA)/poly(ethylene glycol)$_{700}$ diacrylate composition in the presence and absence of the gas producing component.

The biostable foam was prepared according to Example 46. The biostable solid A was prepared according to Example 46 but without the potassium bicarbonate and citric acid.

Results are shown in Table 6.

TABLE 6

| Foam | Weight (g) | L (cm) | W (cm) | H (cm) | Volume ($cm^3$) | Density ($g/cm^3$) |
|---|---|---|---|---|---|---|
| 1 | 0.2446 | 0.951 | 1 | 0.61 | 0.6 | 0.422 |
| 2 | 0.4685 | 1 | 1.01 | 1.07 | 1.1 | 0.434 |
| 3 | 0.465 | 0.95 | 1.11 | 1.1 | 1.2 | 0.401 |
| | | | | | avg | 0.419 |
| | | | | | stdev | 0.017 |

| Solid | Weight (g) | Diameter (cm) | Radius (cm) | H (cm) | Volume ($cm^3$) | Density ($g/cm^3$) |
|---|---|---|---|---|---|---|
| 1 | 1.0733 | 1.214 | 0.607 | 0.9 | 1.0 | 1.031 |
| 2 | 1.2511 | 1.214 | 0.607 | 1 | 1.2 | 1.081 |
| 3 | 1.2112 | 1.214 | 0.607 | 0.96 | 1.1 | 1.091 |
| | | | | | avg | 1.068 |
| | | | | | stdev | 0.032 |

The percent solids in foam A was 39.22%. Pore volume is calculated at 2.59.

What is claimed is:

1. A system for forming a biocompatible biodegradable foam comprising:
   a) a first covalently crosslinkable polymer comprising poly-α(1→4)glucopyranose and pendent free-radically polymerizable groups, wherein the poly-α(1→4)glucopyranose is maltodextrin;
   b) a second covalently crosslinkable polymer comprising an alkylene oxide polymer comprising pendent polymerizable groups;
   c) a polymerization initiator; and
   d) a gas-producing component comprising a bicarbonate salt and a biocompatible acid.

2. The system of claim 1 wherein the polymerizable groups are pendent from the poly-α(1→4)glucopyranose in an amount in the range of 0.05 mmol/gram to 0.4 mmol/gram (polymerizable groups/poly-α(1→4)glucopyranose).

3. The system of claim 2 wherein the polymerizable groups are pendent from the poly-α(1→4)glucopyranose in an amount in the range of 0.1 mmol/gram to about 0.35 mmol/gram (polymerizable groups/poly-α(1→4)glucopyranose).

4. The system of claim 1 wherein the covalently crosslinkable polymer comprising poly-α(1→4)glucopyranose has a molecular weight of 500,000 Da or less.

5. The system of claim 1 having a ratio of the first covalently crosslinkable polymer comprising poly-α(1→4)glucopyranose to the second covalently crosslinkable polymer in the range of 1:1 to 3:1 by weight.

6. The system of claim 1 wherein the polymerization initiator comprises a peroxide-based initiator.

7. The system of claim 1 further comprising a poloxamer surfactant.

8. The system of claim 1 comprising a first liquid composition in which the covalently crosslinkable polymer comprising poly-α(1→4)glucopyranose is present at a concentration in the range of 200 mg/mL to 1000 mg/mL.

9. The system of claim 8 wherein the covalently crosslinkable polymer comprising poly-α(1→4)glucopyranose is present at a concentration in the range of 400 mg/mL to 700 mg/mL.

10. The system of claim 1 comprising a first liquid composition comprising a first member of a redox pair at a concentration in the range of 2.0 mM to 25 mM.

11. The system of claim 1 comprising a first liquid composition comprising the biocompatible acid at a concentration in the range of 20 mg/mL to 80 mg/mL.

12. The system of claim 1 comprising a second liquid composition comprising a second member of a redox pair at a concentration in the range of 2.0 mM to 25 mM.

13. The system of claim 1 comprising a second liquid composition comprising the bicarbonate salt at a concentration in the range of 20 mg/mL to 80 mg/mL.

14. The system of claim 1 comprising a second liquid composition including the second covalently crosslinkable polymer at a concentration in the range of 100 mg/mL to 500 mg/mL.

15. The system of claim 1 comprising a first liquid composition comprising ferrous lactate at a concentration in the range of 4 mM to 30 mM, citric acid at a concentration in the range of 60 mg/mL to 120 mg/mL, and the covalently crosslinkable polymer comprising poly-α(1→4)glucopyranose and pendent polymerizable groups at a concentration in the range of 500 mg/mL to 700 mg/mL, and a second liquid composition comprising hydrogen peroxide at a concentration in the range of 4 mM to 30 mM, potassium bicarbonate at a concentration in the range of 60 mg/mL to 120 mg/mL, and the second covalently crosslinkable polymer at a concentration in the range of 350 mg/mL to 550 mg/mL.

16. The system of claim 1 wherein the pendent free radically polymerizable groups are selected from the group consisting of acrylate, methacrylate, ethacrylate, 2-phenyl acrylate, acrylamide, methacrylamide, itaconate groups, and styrene.

17. The system of claim 1 wherein the polymerization initiator comprises an activating component that is a $Fe^{2+}$-based activator.

18. The system of claim 17 wherein the polymerization initiator comprises an activating component selected from the group consisting of ferrous gluconate, ferrous ascorbate, ferrous acetylacetonate, and ferrous lactate.

19. The system of claim 1 wherein the system comprises an aqueous liquid, and the first and second covalently crosslinkable polymers, the polymerization initiator, and the gas-producing component are dissolvable in the aqueous liquid.

20. A system for forming a biocompatible biodegradable foam comprising:
   a) a first covalently crosslinkable polymer comprising a linear poly-α(1→4)glucopyranose having a molecular weight of 500,000 Da or less and comprising pendent free radically polymerizable groups;
   b) a second covalently crosslinkable polymer comprising an alkylene oxide polymer comprising pendent polymerizable groups;
   c) a $Fe^{2+}$-based activator;
   d) a biocompatible acid; and
   e) a bicarbonate salt.

21. A system for forming a biocompatible biodegradable foam comprising:
   a) a first covalently crosslinkable polymer comprising poly-α(1→4)glucopyranose and pendent free-radically polymerizable groups;
   b) a second covalently crosslinkable polymer comprising an alkylene oxide polymer comprising pendent polymerizable groups;
   c) a polymerization initiator; and
   d) a water-soluble gas-producing component comprising a bicarbonate salt and a biocompatible acid;
   wherein the first and second covalently crosslinkable polymers, polymerization initiator, and gas-producing component are dissolvable in a physiologically compatible aqueous composition having a pH in the range of about 6.5 to about 7.5.

22. The system of claim 21 wherein the water-soluble gas-producing component is present in an amount sufficient to cause formation of pores in the biocompatible biodegradable foam when combined with the polymer and polymerization initiator.

23. The system of claim 21 wherein the first covalently crosslinkable polymer comprising poly-α(1→4)glucopyranose has a molecular weight of 500,000 Da or less.

* * * * *